(12) United States Patent
Weis

(10) Patent No.: US 9,549,935 B2
(45) Date of Patent: Jan. 24, 2017

(54) METHODS AND COMPOSITIONS FOR TREATING MIGRAINES USING NORIBOGAINE

(71) Applicant: DemeRx, Inc., Fort Lauderdale, FL (US)

(72) Inventor: Holger Weis, Fort Lauderlale, FL (US)

(73) Assignee: DEMERX, INC., Fort Lauderdale, FL (US)

( * ) Notice: Subject to any disclaimer, the term of this patent is extended or adjusted under 35 U.S.C. 154(b) by 0 days.

(21) Appl. No.: 14/624,292

(22) Filed: Feb. 17, 2015

(65) Prior Publication Data

US 2016/0008372 A1 Jan. 14, 2016

Related U.S. Application Data

(60) Provisional application No. 62/024,388, filed on Jul. 14, 2014.

(51) Int. Cl.
*A61K 31/55* (2006.01)
*A61K 45/06* (2006.01)

(52) U.S. Cl.
CPC .............. *A61K 31/55* (2013.01); *A61K 45/06* (2013.01)

(58) Field of Classification Search
CPC ................................ A61K 31/55; A61K 45/06
USPC ..................................................... 514/214.02
See application file for complete search history.

(56) References Cited

U.S. PATENT DOCUMENTS

| | | | |
|---|---|---|---|
| 4,626,539 A | 12/1986 | Aungst et al. | |
| 4,806,341 A | 2/1989 | Chien et al. | |
| 5,149,538 A | 9/1992 | Granger et al. | |
| 5,591,738 A | 1/1997 | Lotsof | |
| 5,616,575 A | 4/1997 | Efange et al. | |
| 6,348,456 B1 | 2/2002 | Mash et al. | |
| 6,416,793 B1 | 7/2002 | Zeligs et al. | |
| 6,933,308 B2 * | 8/2005 | Boy ..................... | C07D 277/56 514/231.5 |
| 7,220,737 B1 | 5/2007 | Mash | |
| 7,754,710 B2 | 7/2010 | Mash | |
| 8,178,524 B2 | 5/2012 | Mash | |
| 8,362,007 B1 | 1/2013 | Mash et al. | |
| 8,637,648 B1 | 1/2014 | Mash et al. | |
| 8,741,891 B1 | 6/2014 | Mash | |
| 8,765,737 B1 | 7/2014 | Mash et al. | |
| 8,853,201 B2 | 10/2014 | Gless et al. | |
| 9,045,481 B2 * | 6/2015 | Mash ................... | C07D 471/22 |
| 2003/0153552 A1 | 8/2003 | Mash et al. | |
| 2003/0194438 A1 | 10/2003 | Prescott et al. | |
| 2006/0229293 A1 | 10/2006 | Lotsof | |
| 2007/0185085 A1 | 8/2007 | Mash | |
| 2010/0311722 A1 | 12/2010 | Mash | |
| 2010/0311723 A1 | 12/2010 | Mash | |
| 2010/0311725 A1 | 12/2010 | Mash | |
| 2012/0083485 A1 | 4/2012 | Mash | |
| 2012/0253037 A1 | 10/2012 | Moriarty et al. | |
| 2013/0011444 A1 | 1/2013 | Zebala | |
| 2013/0131046 A1 | 5/2013 | Moriarty et al. | |
| 2013/0165414 A1 | 6/2013 | Gless et al. | |
| 2013/0165425 A1 | 6/2013 | Gless et al. | |
| 2013/0165647 A1 | 6/2013 | Moriarty et al. | |
| 2013/0211073 A1 | 8/2013 | Moriarty | |
| 2013/0211074 A1 | 8/2013 | Moriarty | |
| 2013/0296823 A1 | 11/2013 | Melker et al. | |
| 2013/0303756 A1 | 11/2013 | Mash et al. | |
| 2014/0179685 A1 | 6/2014 | Mash et al. | |
| 2014/0288056 A1 | 9/2014 | Friedhoff | |
| 2014/0315891 A1 | 10/2014 | Mash | |
| 2014/0357741 A1 | 12/2014 | Mash et al. | |
| 2015/0231146 A1 | 8/2015 | Friedhoff | |
| 2015/0238503 A1 | 8/2015 | Maillet et al. | |
| 2015/0246055 A1 | 9/2015 | Friedhoff | |
| 2015/0257667 A1 | 9/2015 | Friedhoff | |
| 2015/0258105 A1 | 9/2015 | Maillet et al. | |
| 2015/0258106 A1 | 9/2015 | Friedhoff | |
| 2015/0258107 A1 | 9/2015 | Friedhoff | |
| 2015/0258108 A1 | 9/2015 | Maillet et al. | |
| 2015/0258111 A1 | 9/2015 | Maillet et al. | |
| 2015/0258113 A1 | 9/2015 | Friedhoff | |
| 2015/0258114 A1 | 9/2015 | Friedhoff | |
| 2015/0342959 A1 | 12/2015 | Friedhoff | |
| 2016/0038508 A1 | 2/2016 | Perry et al. | |
| 2016/0220579 A1 | 8/2016 | Weis et al. | |

FOREIGN PATENT DOCUMENTS

| | | |
|---|---|---|
| WO | WO-96/03127 A1 | 2/1996 |
| WO | WO-99/11250 | 3/1999 |
| WO | WO-2012/012764 A1 | 1/2012 |
| WO | WO-2012/103028 | 8/2012 |
| WO | WO-2012/135047 | 10/2012 |
| WO | WO-2013/040471 | 3/2013 |
| WO | WO-2013/085849 | 6/2013 |

(Continued)

OTHER PUBLICATIONS

U.S. Appl. No. 13/593,454, filed Aug. 23, 2012, Moriarty et al.
U.S. Appl. No. 14/292,632, filed May 30, 2014, Friedhoff, Lawrence.
U.S. Appl. No. 61/852,485, filed Mar. 15, 2013, Friedhoff, Lawrence.
Australian New Zealand Clinical Trials Registry ACTRN12612000821897, 2012.
Calsyn et al., "Slow tapering from methadone maintenance in a program encouraging indefinite maintenance," Journal of Substance Abuse Treatment, (2006), 30:159-163.
Donnelly, J.R., "The Need for Ibogaine in Drug and Alcohol Addiction Treatment," Journal of Legal Medicine, (2011), 32:93-114.
Eap et al., "Interindividual Variability of the Clinical Pharmacokinetics of Methadone," Clinical Pharmacokinetics, (2002), 41(14):1153-1193.

(Continued)

*Primary Examiner* — Jennifer M Kim
(74) *Attorney, Agent, or Firm* — Foley & Lardner LLP

(57) ABSTRACT

This invention provides methods and compositions for treating or preventing migraine headache and/or symptoms thereof in a subject. The method comprises administering to the subject in need thereof a therapeutically effective amount of noribogaine, noribogaine derivative, or a pharmaceutically acceptable salt thereof.

15 Claims, 9 Drawing Sheets

(56) References Cited

FOREIGN PATENT DOCUMENTS

| WO | WO-2013/085922 A1 | 6/2013 |
|---|---|---|
| WO | WO-2013/112622 | 8/2013 |
| WO | WO-2013/112673 | 8/2013 |
| WO | WO-2014/019692 | 2/2014 |
| WO | WO-2014/143201 | 9/2014 |
| WO | WO-2014/144508 | 9/2014 |
| WO | WO-2015/126434 | 8/2015 |
| WO | WO-2015/126836 | 8/2015 |
| WO | WO-2015/195673 | 12/2015 |
| WO | WO-2016/086194 | 6/2016 |
| WO | WO-2016/134019 | 8/2016 |

OTHER PUBLICATIONS

Huffman et al., "A Formal Synthesis of (±)-Ibogamine", J. Org. Chem., (1985), 50:1460-1464.
Khan et al., "Long QT syndrome: Diagnosis and management", American Heart Journal, 2002, 143(1):7-14.
Krantz, et al., "QTC Interval Screen in Methadone Treatment," Annals of Internal Medicine, 2009, American College of Physicians, vol. 150, pp. 387-395.
Kubiliene, et al., "Acute toxicity of ibogaine and noribogaine," Medicina (Kaunas), (2008), 44(12):984-988.
Mitchell et al., "Temperature and the cold pressor test", J. Pain, 2004, 5:233-237.
PCT International Search Report and Written Opinion dated Mar. 10, 2014 in related PCT Patent Application No. PCT/US13/69235.
PCT International Search Report and Written Opinion for Appl No. PCT/US2015/016186 dated Apr. 24, 2015 5 Pages.
PCT International Search Report and Written Opinion for Appl. No. PCT/US2014/019692 dated Nov. 18, 2014.
Pearl et al., "Radioligand-binding Study of Noribogaine, A Likely Metabolite of Ibogaine", Brain Research, 1995, 675:342-344.
Weiss et al., "Neurobiology of craving, conditioned reward and relapse", Current Opinion in Pharmacology, 2005, 5:9-19.
Zubaran et a., "Noribogaine Generalization to the Ibogaine Stimulus: Correlation with Noribogaine Concentration in Rat Brain", Neuropsychopharmacology, 1999, vol. 21, pp. 119-126.
International Preliminary Report on Patentability dated Sep. 24, 2015 for PCT Application No. PCT/US2014/028946.
International Preliminary Report on Patentability for PCT/US2013/069235, mailed Sep. 15, 2005.
Maillet et al., "Noribogaine is a G-protein biased k-opiod receptor agonist", Neuropharmacology, 2015, 99, pp. 675-688.
Stichering, Christian, Methadone-induced Torsade de pointes tachycardias, Swiss Med Wkly, 2005; vol. 135, pp. 282-285.
Bhargava, et al.,"Effects of ibogaine and noribogaine on the antinociceptive action of μ-, δ- and k-opioid receptor agonists in mice," Brain Research, (1997), 752:234-238.
Cao, et al., "Effects of ibogaine on the development of tolerance to antinociceptive action of μ-, δ- and k-opioid receptor agonists in mice," Brain Research, (1997), 752:250-254.
Goutarel, et al., "Pharmacodynamics and Therapeutic Applications of Iboga and Ibogaine," Psychedelic Monographs and Essays, vol. 6:70-111, 1993.
International Search Report and Written Opinion Application No. PCT/US2015/062783, mail date Feb. 9, 2016, 16 pages.
Kroupa, et al., "Ibogaine in the 21st Century: Boosters, Tune-ups and Maintenance," Maps, (2005), 15(1):21-24.
New Zealand Ministry of Health, Prescriber Update (2010), 31(4), pp. 27-29.
PCT International Preliminary Report on Patentability for PCT Patent Application No. PCT/US14/19692, dated Feb. 1, 2016. 19 pages.
PCT International Search Report and Written Opinion for Appl. No. PCT/US2014/028946, dated Jul. 28, 2014.
Popik et. al. "100 Years of Ibogaine: Neourochemical and Pharmacological Actions of a Putative Anti-addictive Drug." Pharmacological Reviews (1995)47:235:253.
Sharma et. al. "Enhancement of Morphine Antinociception by Ibogaine and Noribogaine in Morphine-tolerant Mice," Pharmacology (1998) 57:229-232.
Hoelen, et al., "Long-QT Syndrome Induced by the Antiaddiction Drug Ibogaine", New England Journal of Medicine, 2009, pp. 307-308.
PCT International Search Report dated Aug. 12, 2016 in related PCT Patent Application No. PCT/US2016/031932.
Chang et al. "Noribogaine reduces nicotine self-administration in rats," Journal of Pyschopharmacology, 20 May 2015, vol. 29, No. 6, pp. 704-711.
Malik et al., "Evaluation of Drug-Induced QT Interval Prolongation," Drug Safety, 2001, 24(5), pp. 323-351.
PCT International Search Report and Written Opinion dated Jun. 10, 2016 in related PCT Patent Application No. PCT/US16/18273.

* cited by examiner

Box includes values representing 25% - 75% quartiles. Diamond = median; crossbar in box = mean; whiskers = values within standard deviation of mid-quartiles. No outliers present.

METHODS AND COMPOSITIONS FOR TREATING MIGRAINES USING NORIBOGAINE

CROSS-REFERENCE TO RELATED APPLICATIONS

This application claims benefit from U.S. Provisional Application No. 60/024,388, filed Jul. 14, 2014, which is hereby incorporated by reference in its entirety.

FIELD OF THE INVENTION

This invention relates generally to methods and compositions for the treatment and/or prevention of migraine headaches and/or symptoms thereof by administering noribogaine, a noribogaine derivative, or a pharmaceutically acceptable salt or solvate thereof. This invention further relates generally to methods and compositions for the treatment and/or prevention of migraines by administering noribogaine, a noribogaine derivative, or a pharmaceutically acceptable salt or solvate thereof in conjunction with an agent to treat migraines.

STATE OF THE ART

Noribogaine is sometimes referred to as 12-hydroxyibogaine. Noribogaine can be depicted by the following formula:

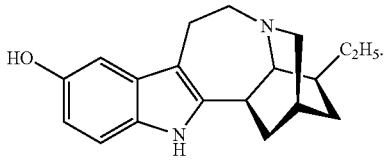

Noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737). Such treatment generally requires administration of high doses of noribogaine, typically 0.1 mg to 100 mg per kg body weight.

Noribogaine is a metabolite of ibogaine found in human, dog, rat and monkey. While the prior art suggests that ibogaine at higher doses is useful as a treatment for addiction, use of ibogaine is associated with hallucinations and other negative side effects. In the United States, ibogaine is classified as a Schedule I controlled substance. Noribogaine has been suggested to have a greater and longer lasting activity in humans than ibogaine for reducing craving for addictive substances and treating chemical dependency. U.S. Pat. No. 6,348,456, incorporated by reference herein in its entirety, discloses highly purified noribogaine and teaches that it should be provided at dosages from about 0.01 to about 100 mg per kg body weight per day to treat addiction, although no human data was provided showing an effective dose to treat drug addiction.

The therapeutic dosing of noribogaine for long-term treatment in humans has not previously been addressed, especially as it relates to dosing protocols that are effective, as well as safe. Indeed, prior to the instant invention, it was uncertain as to whether noribogaine could be administered at a dose which was therapeutic while at the same time safe for patients.

Migraine headaches (also referred to as "headaches") are a neurological disorder whose symptoms include headaches of moderate to severe intensity, which may be accompanied by nausea, vomiting, sensitivity to sensory inputs (light, sound, and/or smell), fatigue, irritability, and/or auras. Migraines can last for prolonged periods of time, usually between 4 and 72 hours. Migraines affect approximately 15% of the human population, with up to 2.2% of the population experiencing chronic migraines. Costs associated with migraines (e.g., patient care, lost productivity, etc.) in the U.S. are estimated to be up to $17 billion per year.

Migraines are generally managed by trigger avoidance, control of symptoms, and prevention using pharmacologic agents. Acupuncture, acupressure, massage, and relaxation may also be used. Biofeedback, neurostimulators, or migraine surgery may be used in more severe cases, especially those that do not respond to other treatments.

Given the prevalence of migraines and the difficulty in treatment and/or prevention, there remains an acute need for effective strategies for treating and preventing migraines and symptoms thereof.

SUMMARY

The current invention is predicated, in part, on the surprising discovery that treatment with a narrow dosage range of noribogaine, noribogaine derivative, or pharmaceutically acceptable salt and/or solvate thereof, of between about 1 mg/kg body weight and about 4 mg/kg body weight, provides a therapeutic alleviation of migraine headaches. Preferably, the dose provides both therapeutic results and an acceptable QT interval prolongation of less than about 50 milliseconds (ms) in humans.

This invention is based, in part, on the discovery that noribogaine reduces frequency, severity, and/or length of headaches, and particularly migraine headaches. This invention is further based on the discovery that at very low doses, direct blood stream delivery of noribogaine can treat and/or prevent migraine headaches. Direct blood stream delivery of noribogaine enhances the amount of noribogaine delivered to the brain, because noribogaine so administered does not initially pass through the liver before reaching the brain as it does when ingested. Direct blood stream delivery of noribogaine includes sublingual, buccal, pulmonary and intranasal delivery, where the noribogaine is absorbed directly into the blood stream for delivery into the brain. The rapid delivery of noribogaine into the brain may cause a significant reduction in the symptoms of migraine, typically less than 15 minutes after administration.

Migraine headaches may contain four phases, although not all phases are experienced in all cases. The first phase is the prodrome phase, wherein the patient experiences irritability, altered mood, depression or euphoria, fatigue, food cravings, muscle stiffness, constipation or diarrhea, and sensitivity to smells and/or noise. The second phase is the aura phase, characterized by visual, sensory, or motor effects. Only a subset of migraines include auras. The third phase is the pain phase; pain is often accompanied by nausea, vomiting, sensitivity to sensory input, fatigue, irritability, vertigo, light-headedness, confusion, blurred vision, nasal stuffiness, diarrhea, frequent urination, pallor, or sweating. The final phase is the postdrome phase, and may include a sore feeling at the site of the migraine, impaired thinking, fatigue, head pain, mood changes, gastrointestinal symptoms, and weakness.

The cause of migraines is unclear, but migraines can be brought on by triggers, including hormone changes, stress, hunger, fatigue, certain smells, foods, poor air quality, etc. Migraine may also be affected by genetic factors.

In one aspect, this invention relates to methods of treating or preventing migraines and/or symptoms thereof, comprising administration of a therapeutic amount of noribogaine. As used herein, unless specified otherwise, noribogaine includes noribogaine, a noribogaine derivative, or a pharmaceutically acceptable salt of each thereof. In one embodiment, the patient is co-administered a therapeutic amount of an agent known to treat migraines in addition to noribogaine. In a preferred embodiment, the co-treatment does not result in a QT interval prolongation of greater than 50 ms. In one embodiment, both compounds are administered at the same time. In one embodiment, the compounds are administered at different times (e.g., sequentially).

In one aspect, this invention relates to treating migraines and/or symptoms thereof in a patient in need thereof, comprising administering to the patient by direct blood stream delivery a therapeutically effective amount of noribogaine or derivative. In one aspect, a therapeutically effective amount of noribogaine or derivative is from about 50 ng to about 10 µg per kg of body weight. In some embodiments, the therapeutically effective amount of noribogaine or noribogaine derivative is administered once a day, twice a day, or more than twice a day. In one embodiment, an agent known to treat and/or prevent migraines is also administered.

In another aspect, this invention provides a method for treating migraines and/or symptoms thereof in a patient in need thereof, comprising administering to the patient a therapeutic amount of noribogaine or a noribogaine derivative or pharmaceutically acceptable salt thereof, wherein the noribogaine or derivative or pharmaceutically acceptable salt thereof is administered by sublingual, intranasal, buccal, or intrapulmonary delivery.

This invention relates to methods of preventing migraines and/or symptoms thereof, comprising administration of a prophylactic amount of noribogaine to prevent or ameliorate migraine and/or symptoms thereof. As used herein, unless specified otherwise, noribogaine includes noribogaine, a noribogaine derivative, or a pharmaceutically acceptable salt of each thereof. In one embodiment, an agent known to treat and/or prevent migraines is also administered.

In one aspect, this invention relates to preventing migraines and/or symptoms thereof in a patient in need thereof, comprising administering to the patient by direct blood stream delivery a prophylactically effective amount of noribogaine. In one aspect, a prophylactically effective amount of noribogaine is from about 1 mg to about 2 mg per kg of body weight. In one aspect, a prophylactically effective amount of noribogaine is from about 50 ng to about 10 µg per kg of body weight. In some embodiments, the prophylactically effective amount of noribogaine or noribogaine derivative is administered once a day, twice a day, or more than twice a day. In some embodiments, the prophylactically effective amount is administered regularly (e.g., every day). In some embodiments, the prophylactically effective amount is administered prior to, concurrent with, or immediately after potential triggers for migraine. In some embodiments, the prophylactically effective amount is administered when the patient feels the onset of at least one symptom of migraine. In one embodiment, an agent known to treat and/or prevent migraines is also administered.

In another aspect, this invention provides a method for preventing migraines and/or symptoms thereof in a patient in need thereof, comprising administering to the patient a prophylactically effective amount of noribogaine, a noribogaine derivative, or a pharmaceutically acceptable salt or solvate thereof, wherein the noribogaine, derivative, or salt thereof is administered by sublingual, intranasal, buccal, or intrapulmonary delivery.

In another aspect, this invention provides a compound for treating and/or preventing migraines, comprising a therapeutic or prophylactic amount of noribogaine, a noribogaine derivative, or a pharmaceutically acceptable salt or solvate thereof, at least one agent that is known to treat and/or prevent migraines, and optionally a pharmaceutically acceptable excipient.

DETAILED DESCRIPTION

Figure 1:
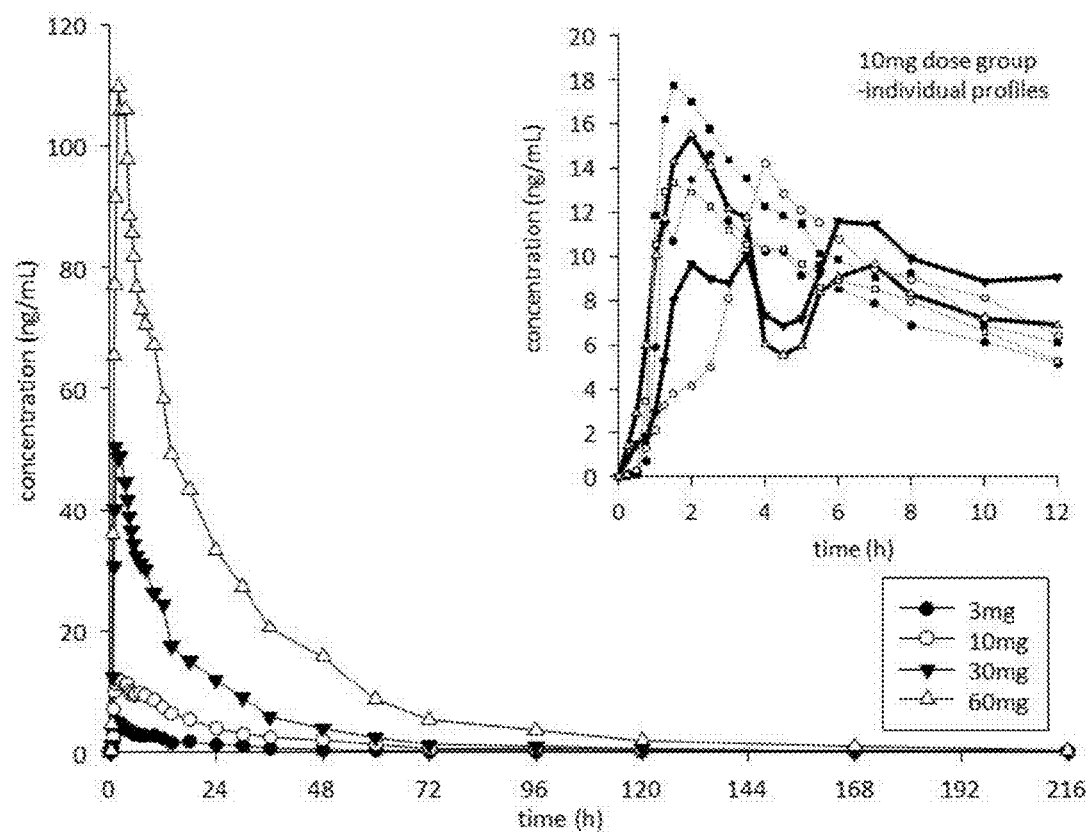
FIG. 1 represents mean noribogaine concentration-time profiles in healthy patients after single oral dosing with 3, 10, 30 or 60 mg doses. Inset: Individual concentration-time profiles from 0-12 h after a 10 mg dose.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a compound" includes a plurality of compounds.

I. DEFINITIONS

Unless defined otherwise, all technical and scientific terms used herein have the same meaning as commonly understood by one of ordinary skill in the art to which this invention belongs. As used herein the following terms have the following meanings.

The term "about" when used before a numerical designation, e.g., temperature, time, amount, concentration, and such other, including a range, indicates approximations which may vary by (+) or (−) 20%, 10%, 5%, 1%, or any subrange or subvalue there between. Preferably, the term "about" when used with regard to a dose amount means that the dose may vary by +/−20%. For example, "about 2 mg/kg noribogaine" indicates that a patient may be administered a dose of noribogaine between 1.6 mg/kg and 2.4 mg/kg. In another example, about 120 mg per unit dose of noribogaine indicates that the unit dose may range from 96 mg to 144 mg.

"Administration" refers to introducing an agent, such as noribogaine, into a patient. Typically, an effective amount is administered, which amount can be determined by the treating physician or the like. Any route of administration, such as oral, topical, subcutaneous, peritoneal, intra-arterial, inhalation, vaginal, rectal, nasal, introduction into the cerebrospinal fluid, or instillation into body compartments can be used. The agent, such as noribogaine, may be administered by direct blood stream delivery, e.g. sublingual, buccal, intranasal, or intrapulmonary administration.

The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient.

"Periodic administration" or "periodically administering" refers to multiple treatments that occur on a daily, weekly, or monthly basis. Periodic administration may also refer to administration of an agent, such as noribogaine, noribogaine derivative, or salt or solvate thereof one, two, three, or more times per day. Administration may be via transdermal patch, gum, lozenge, sublingual tablet, intranasal, intrapulmonary, oral administration, or other administration.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, the term "alkyl" refers to monovalent saturated aliphatic hydrocarbyl groups having from 1 to 12 carbon atoms, 1 to 10 carbon atoms, preferably 1 to 6 carbon atoms, and more preferably 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3$)($CH_3CH_2$)CH—), t-butyl (($CH_3)_3C$—), n-pentyl ($CH_3CH_2CH_2CH_2CH_2$—), and neopentyl (($CH_3)_3CCH_2$—). The term "$C_x$ alkyl" refers to an alkyl group having x carbon atoms, wherein x is an integer, for example, $C_3$ refers to an alkyl group having 3 carbon atoms.

"Alkenyl" refers to straight or branched hydrocarbyl groups having from 2 to 6 carbon atoms and preferably 2 to 4 carbon atoms and having at least 1 and preferably from 1 to 2 sites of vinyl (>C═C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH₂C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{38}$C(O)alkyl, —$NR^{38}$C(O)substituted alkyl, —$NR^{38}$C(O)cycloalkyl, —$NR^{38}$C(O)substituted cycloalkyl, —$NR^{38}$C(O)cycloalkenyl, —$NR^{38}$C(O)substituted cycloalkenyl, —$NR^{38}$C(O)alkenyl, —$NR^{38}$C(O)substituted alkenyl, —$NR^{38}$C(O)alkynyl, —$NR^{38}$C(O)substituted alkynyl, —$NR^{38}$C(O)aryl, —$NR^{38}$C(O)substituted aryl, —$NR^{38}$C(O)heteroaryl, —$NR^{38}$C(O)substituted heteroaryl, —$NR^{38}$C(O)heterocyclic, and —$NR^{38}$C(O)substituted heterocyclic wherein $R^{38}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{39}R^{40}$ where $R^{39}$ and $R^{40}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{39}$ and $R^{40}$ are optionally joined, together with the nitrogen bound thereto to form a heterocyclic or substituted heterocyclic group, provided that $R^{39}$ and $R^{40}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{39}$ is hydrogen and $R^{40}$ is alkyl, the substituted amino group is sometimes referred to herein as alkylamino. When $R^{39}$ and $R^{40}$ are alkyl, the substituted amino group is sometimes referred to herein as dialkylamino. When referring to a monosubstituted amino, it is meant that either $R^{39}$ or $R^{40}$ is hydrogen but not both. When referring to a disubstituted amino, it is meant that neither $R^{39}$ nor $R^{40}$ are hydrogen.

"Aminocarbonyl" refers to the group —C(O)$NR^{41}R^{42}$ where $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)NR$^{41}$R$^{42}$ where $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{38}$C(O)NR$^{41}$R$^{42}$ where $R^{38}$ is hydrogen or alkyl and $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^{38}$C(S)NR$^{41}$R$^{42}$ where $R^{38}$ is hydrogen or alkyl and $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)NR$^{41}$R$^{42}$ where $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —SO$_2$NR$^{41}$R$^{42}$ where $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —O—SO$_2$NR$^{41}$R$^{42}$ where $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{38}$—SO$_2$NR$^{41}$R$^{42}$ where $R^{38}$ is hydrogen or alkyl and $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{43}$)NR$^{41}$R$^{42}$ where $R^{41}$, $R^{42}$, and $R^{43}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR$^{38}$—C(O)O-alkyl, —NR$^{38}$—C(O)O-substituted alkyl, —NR$^{38}$—C(O)O-alkenyl, —NR$^{38}$—C(O)O-substituted alkenyl, —NR$^{38}$—C(O)O-alkynyl, —NR$^{38}$—C(O)O-substituted alkynyl, —NR$^{38}$—C(O)O-aryl, —NR$^{38}$—C(O)O-substituted aryl, —NR$^{38}$—C(O)O-cycloalkyl, —NR$^{38}$—C(O)O-substituted cycloalkyl, —NR$^{38}$—C(O)O-cycloalkenyl, —NR$^{38}$—C(O)O-substituted cycloalkenyl, —NR$^{38}$—C(O)O-heteroaryl, —NR$^{38}$—C(O)O-substituted heteroaryl, —NR$^{38}$—C(O)O-heterocyclic, and —NR$^{38}$—C(O)O-substituted heterocyclic wherein R$^{38}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. One or more of the rings can be aryl, heteroaryl, or heterocyclic provided that the point of attachment is through the non-aromatic, non-heterocyclic ring carbocyclic ring. Examples of suitable cycloalkyl groups include, for instance, adamantyl, cyclopropyl, cyclobutyl, cyclopentyl, and cyclooctyl. Other examples of cycloalkyl groups include bicycle[2,2,2]octanyl, norbornyl, and spirobicyclo groups such as spiro[4.5]dec-8-yl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{44}$C(=NR$^{44}$)N(R$^{44}$)$_2$ where each R$^{44}$ is independently selected from the group consisting of hydrogen, alkyl, substituted alkyl, aryl, substituted aryl, heteroaryl, substituted heteroaryl, heterocyclic, and substituted heterocyclic and two R$^{44}$ groups attached to a common guanidino nitrogen atom are optionally joined together with the nitrogen bound thereto to form a heterocyclic or substituted heterocyclic group, provided that at least one R$^{44}$ is not hydrogen, and wherein said substituents are as defined herein.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Haloalkoxy" refers to alkoxy groups substituted with 1 to 5, 1 to 3, or 1 to 2 halo groups, wherein alkoxy and halo are as defined herein.

"Haloalkylthio" refers to alkylthio groups substituted with 1 to 5, 1 to 3, or 1 to 2 halo groups, wherein alkylthio and halo are as defined herein.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridyl, pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, and/or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic heterocyclic ring. In one embodiment, the nitrogen and/or sulfur atom(s) of the heterocyclic group are optionally oxidized to provide for the N-oxide, sulfinyl, and/or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O) or (—O$^-$).

"Spiro ring systems" refers to bicyclic ring systems that have a single ring carbon atom common to both rings.

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl-SO$_2$—, phenyl-SO$_2$—, and 4-methylphenyl-SO$_2$—. The term "alkylsulfonyl" refers to —SO$_2$-alkyl. The term "haloalkylsulfonyl" refers to —SO$_2$-haloalkyl where haloalkyl is defined herein. The term "(substituted sulfonyl) amino" refers to —NH(substituted sulfonyl), and the term "(substituted sulfonyl)aminocarbonyl" refers to —C(O)NH (substituted sulfonyl), wherein substituted sulfonyl is as defined herein.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cycloalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

"Compound" or "compounds" as used herein is meant to include the stereoiosmers and tautomers of the indicated formulas.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

As used herein, the term "phosphate ester" refers to any one of the mono-, di- or triphosphate esters of noribogaine, wherein the mono-, di- or triphosphate ester moiety is bonded to the 12-hydroxy group and/or the indole nitrogen of noribogaine.

As used herein, the term "phosphate ester" refers to any one of the mono-, di- or triphosphate esters of noribogaine, wherein the mono-, di- or triphosphate ester moiety is bonded to the 12-hydroxy group and/or the indole nitrogen of noribogaine.

As used herein, the term "monophosphate" refers to the group —P(O)(OH)$_2$.

As used herein, the term "diphosphate" refers to the group —P(O)(OH)—OP(O)(OH)$_2$.

As used herein, the term "triphosphate" refers to the group —P(O)(OH)—(OP(O)(OH))$_2$OH.

As used herein, the term "ester" as it refers to esters of the mono-, di- or triphosphate group means esters of the monophosphate can be represented by the formula —P(O)(OR$^{45}$)$_2$, where each R$^{45}$ is independently hydrogen, $C_1$-$C_{12}$ alkyl, $C_3$-$C_{10}$ cycloalkyl, $C_6$-$C_{14}$ aryl, heteroaryl of 1 to 10 carbon atoms and 1 to 4 optionally oxidized heteroatoms selected from the group consisting of oxygen, nitrogen, and sulfur and the like, provided that at least one R$^{45}$ is not hydrogen. Likewise, exemplary esters of the di- or triphosphate can be represented by the formulas —P(O)(OR$^{45}$)—OP(O)(OR$^{45}$)$_2$ and —P(O)(OR$^{45}$)—(OP(O)(OR$^{45}$))$_2$OR$^{45}$, where R$^{45}$ is as defined above.

As used herein, the term "hydrolyzable group" refers to a group that can be hydrolyzed to release the free hydroxy group under hydrolysis conditions. Examples of hydrolysable group include, but are not limited to those defined for R above. Preferred hydrolysable groups include carboxyl esters, phosphates and phosphate esters. The hydrolysis may be done by chemical reactions conditions such as base hydrolysis or acid hydrolysis or may be done in vivo by biological processes, such as those catalyzed by a phosphate hydrolysis enzyme. Nonlimiting examples of hydrolysable group include groups linked with an ester-based linker (—C(O)O— or —OC(O)—), an amide-based linker (—C(O)NR$^{46}$— or —NR$^{46}$C(O)—), or a phosphate-linker (—P(O)(OR$^{46}$)—O—, —O—P(S)(OR$^{46}$)—O—, —O—P(S)(SR$^{46}$)—O—, —S—P(O)(OR$^{46}$)—O—, —O—P(O)(OR$^{46}$)—S—, —S—P(O)(OR$^{46}$)—S—, —O—P(S)(OR$^{46}$)—S—, —S—P(S)(OR$^{46}$)—O—, —O—P(O)(R$^{46}$)—O—, —O—P(S)(R$^{46}$)—O—, —S—P(O)(R$^{46}$)—O—, —S—P(S)(R$^{46}$)—O—, —S—P(O)(R$^{46}$)—S—, or —O—P(S)(R$^{46}$)—S—) where R$^{46}$ can be hydrogen or alkyl.

"Noribogaine" refers to the compound:

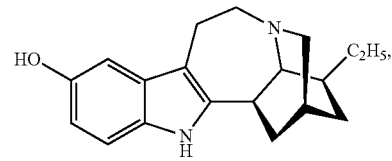

as well as noribogaine derivatives, pharmaceutically acceptable salts thereof, or solvates of each thereof. Noribogaine can be prepared by demethylation of naturally occurring ibogaine:

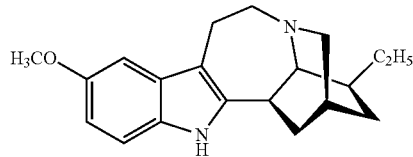

which is isolated from *Tabernanth iboga*, a shrub of West Africa. Demethylation may be accomplished by conventional techniques such as by reaction with boron tribromide/methylene chloride at room temperature followed by conventional purification. See, for example, Huffman, et al., J. Org. Chem. 50:1460 (1985), which incorporated herein by reference in its entirety. Noribogaine can be synthesized as described, for example in U.S. Patent Pub. Nos. 2013/0165647, 2013/0303756, and 2012/0253037, PCT Patent Publication No. WO 2013/040471 (includes description of making noribogaine polymorphs), and U.S. patent application Ser. No. 13/593,454, each of which is incorporated herein by reference in its entirety.

"Noribogaine derivatives" refer to, without limitation, esters or O-carbamates of noribogaine, or solvates of each thereof, or pharmaceutically acceptable salts of each thereof. Also encompassed within this invention are derivatives of noribogaine that act as prodrug forms of noribogaine. A prodrug is a pharmacological substance administered in an inactive (or significantly less active) form. Once administered, the prodrug is metabolized in vivo into an active metabolite. Noribogaine derivatives include, without limitation, those compounds set forth in U.S. Pat. Nos. 6,348,456 and 8,362,007; as well as in U.S. patent application Ser. No. 13/165,626; and US Patent Application Publication Nos. US2013/0131046; US2013/0165647; US2013/0165425; and US2013/0165414; all of which are incorporated herein by reference. Non-limiting examples of noribogaine derivatives encompassed by this invention are given in more detail in the "Compositions" section below.

In some embodiments, the methods of the present disclosure entail the administration of a prodrug of noribogaine that provides the desired maximum serum concentrations and efficacious average noribogaine serum levels. A prodrug of noribogaine refers to a compound that metabolizes, in vivo, to noribogaine. In some embodiments, the prodrug is selected to be readily cleavable either by a cleavable linking arm or by cleavage of the prodrug entity that binds to noribogaine such that noribogaine is generated in vivo. In one preferred embodiment, the prodrug moiety is selected to facilitate binding to the μ and/or κ receptors in the brain either by facilitating passage across the blood brain barrier or by targeting brain receptors other than the μ and/or κ receptors. Examples of prodrugs of noribogaine are provided in U.S. patent application Ser. No. 13/165,626, the entire content of which is incorporated herein by reference.

In one embodiment, the noribogaine derivative is represented by Formula I:

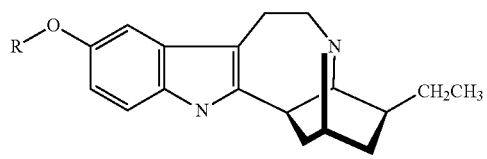

I or a pharmaceutically acceptable salt thereof, wherein R is hydrogen or a hydrolyzable group such as hydrolyzable esters of from about 1 to 12 carbons.

Generally, in the above formula, R is hydrogen or a group of the formula:

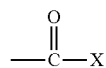

wherein X is a $C_1$-$C_{12}$ group, which is unsubstituted or substituted. For example, X may be a linear alkyl group such as methyl, ethyl, n-propyl, n-butyl, n-pentyl, n-hexyl, n-heptyl, n-octyl, n-nonyl, n-decyl, n-undecyl or n-dodecyl, or a branched alkyl group, such as i-propyl or sec-butyl. Also, X may be a phenyl group or benzyl group, either of which may be substituted with lower alkyl groups or lower alkoxy groups. Generally, the lower alkyl and/or alkoxy groups have from 1 to about 6 carbons. For example, the group R may be acetyl, propionyl or benzoyl. However, these groups are only exemplary.

Generally, for all groups X, they may either be unsubstituted or substituted with lower alkyl or lower alkoxy groups. For example, substituted X may be o-, m- or p-methyl or methoxy benzyl groups.

$C_1$-$C_{12}$ groups include $C_1$-$C_{12}$ alkyl, $C_3$-$C_{12}$ cycloalkyl, $C_6$-$C_{12}$ aryl, $C_7$-$C_{12}$ arylalkyl, wherein $C_x$ indicates that the group contains x carbon atoms. Lower alkyl refers to $C_1$-$C_4$ alkyl and lower alkoxy refers to $C_1$-$C_4$ alkoxy.

In one embodiment, the noribogaine derivative is represented by Formula II:

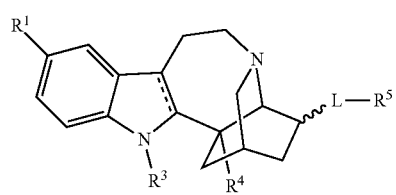

II or a pharmaceutically acceptable salt thereof,
wherein
 ===== is a single or double bond;
$R^1$ is halo, $OR^2$, or $C_1$-$C_{12}$ alkyl optionally substituted with 1 to 5 $R^{10}$;
$R^2$ is hydrogen or a hydrolysable group selected from the group consisting of —C(O)$R^x$, —C(O)O$R^x$ and —C(O)N($R^y$)$_2$ where each $R^x$ is selected from the group consisting of $C_1$-$C_6$ alkyl optionally substituted with 1 to 5 $R^{10}$, and each $R^y$ is independently selected from the group consisting of hydrogen, $C_1$-$C_6$ alkyl optionally substituted with 1 to 5 $R^{10}$, $C_6$-$C_{14}$ aryl optionally substituted with 1 to 5 $R^{10}$, $C_3$-$C_{10}$ cycloalkyl optionally substituted with 1 to 5 $R^{10}$, $C_1$-$C_{10}$ heteroaryl having 1 to 4 heteroatoms and which is optionally substituted with 1 to 5 $R^{10}$, $C_1$-$C_{10}$ heterocyclic having 1 to 4 heteroatoms and which is optionally substituted with 1 to 5 $R^{10}$, and where each $R^y$, together with the nitrogen atom bound thereto form a $C_1$-$C_6$ heterocyclic having 1 to 4 heteroatoms and which is optionally substituted with 1 to 5 $R^{10}$ or a $C_1$-$C_6$ heteroaryl having 1 to 4 heteroatoms and which is optionally substituted with 1 to 5 $R^{10}$;
$R^3$ is selected from the group consisting of hydrogen, $C_1$-$C_{12}$ alkyl optionally substituted with 1 to 5 $R^{10}$, aryl optionally substituted with 1 to 5 $R^{10}$, —C(O)$R^6$, —C(O)N$R^6R^6$ and —C(O)O$R^6$;
$R^4$ is selected from the group consisting of hydrogen, —(CH$_2$)$_m$OR$^8$, —CR$^7$(OH)R$^8$, —(CH$_2$)$_m$CN, —(CH$_2$)$_m$COR$^8$, —(CH$_2$)$_m$CO$_2$R$^8$, —(CH$_2$)$_m$C(O)NR$^7$R$^8$, —(CH$_2$)$_m$C(O)NR$^7$NR$^8$R$^8$, —(CH$_2$)$_m$C(O)NR$^7$NR$^8$C(O)R$^9$, and —(CH$_2$)$_m$NR$^7$R$^8$;
m is 0, 1, or 2;
L is a bond or $C_1$-$C_{12}$ alkylene;
$R^5$ is selected from the group consisting of hydrogen, $C_1$-$C_{12}$ alkyl substituted with 1 to 5 $R^{10}$, $C_1$-$C_{12}$ alkenyl substituted with 1 to 5 $R^{10}$, —X$^1$—R$^7$, —(X$^1$—Y)$_n$—X$^1$—R$^7$, —SO$_2$NR$^7$R$^8$, —O—C(O)R$^9$, —C(O)OR$^8$, —C(O)NR$^7$R$^8$, —NR$^7$R$^8$, —NHC(O)R$^9$, and —NR$^7$C(O)R$^9$;
each $R^6$ is independently selected from the group consisting of hydrogen, $C_1$-$C_{12}$ alkyl, $C_2$-$C_{12}$ alkenyl, $C_2$-$C_{12}$ alkynyl, $C_6$-$C_{10}$ aryl, $C_1$-$C_6$ heteroaryl having 1 to 4 heteroatoms, and $C_1$-$C_6$ heterocycle having 1 to 4 heteroatoms, and wherein the alkyl, alkenyl, alkynyl, aryl, heteroaryl, and heterocycle are optionally substituted with 1 to 5 $R^{10}$;
$X^1$ is selected from the group consisting of O and S;
Y is $C_1$-$C_4$ alkylene or $C_6$-$C_{10}$ arylene, or a combination thereof;
n is 1, 2, or 3;
$R^7$ and $R^8$ are each independently selected from the group consisting of hydrogen, $C_1$-$C_{12}$ alkyl optionally substituted with 1 to 5 $R^{10}$, $C_1$-$C_6$ heterocycle having 1 to 4 heteroatoms and which is optionally substituted with 1 to 5 $R^{10}$, $C_3$-$C_{10}$ cycloalkyl optionally substituted with 1 to 5 $R^{10}$, $C_6$-$C_{10}$ aryl optionally substituted with 1 to 5 $R^{10}$ and $C_1$-$C_6$ heteroaryl having 1 to 4 heteroatoms optionally substituted with 1 to 5 $R^{10}$;

$R^9$ is selected from the group consisting of $C_1$-$C_{12}$ alkyl optionally substituted with 1 to 5 $R^{10}$, $C_1$-$C_6$ heterocycle having 1 to 4 heteroatoms optionally substituted with 1 to 5 $R^{10}$, $C_3$-$C_{10}$ cycloalkyl optionally substituted with 1 to 5 $R^{10}$, $C_6$-$C_{10}$ aryl optionally substituted with 1 to 5 $R^{10}$ and $C_1$-$C_6$ heteroaryl having 1 to 4 heteroatoms optionally substituted with 1 to 5 $R^{10}$;

$R^{10}$ is selected from the group consisting of $C_1$-$C_4$ alkyl, phenyl, halo, —$OR^{11}$, —CN, —$COR^{11}$, —$CO_2R^{11}$, —$C(O)NHR^{11}$, —$NR^{11}R^{11}$, —$C(O)NR^{11}R^{11}$, —$C(O)NHNHR^{11}$, —$C(O)NR^{11}NHR^{11}$, —$C(O)NR^{11}NR^{11}R^{11}$, —$C(O)NHNR^{11}C(O)R^{11}$, —$C(O)NHNHC(O)R^{11}$, —$SO_2NR^{11}R^{11}$, —$C(O)NR^{11}NR^{11}C(O)R^{11}$, and —$C(O)NR^{11}NHC(O)R^{11}$; and $R^{11}$ is independently hydrogen or $C_1$-$C_{12}$ alkyl;

provided that:

when L is a bond, then $R^5$ is not hydrogen;

when ===== is a double bond, $R^1$ is an ester hydrolyzable group, $R^3$ and $R^4$ are both hydrogen, then -L-$R^5$ is not ethyl;

when ===== is a double bond, $R^1$ is —OH, halo or $C_1$-$C_{12}$ alkyl optionally substituted with 1 to 5 $R^{10}$, then $R^4$ is hydrogen; and when ===== is a double bond, $R^1$ is $OR^2$, $R^4$ is hydrogen, -L-$R^5$ is ethyl, then $R^2$ is not a hydrolyzable group selected from the group consisting of an ester, amide, carbonate and carbamate.

In one embodiment, the noribogaine derivative is represented by Formula III:

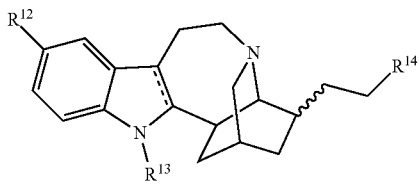

III or a pharmaceutically acceptable salt thereof,
wherein

===== is a single or double bond;

$R^{12}$ is halo, —OH, —SH, —$NH_2$, —$S(O)_2N(R^{17})_2$, —$R^z$-$L^1$-$R^{18}$, —$R^z$-$L^1$-$R^{19}$, —$R^z$-$L^1$-$R^{20}$ or —$R^z$-$L^1$-$CHR^{18}R^{19}$, where $R^z$ is O, S or $NR^{17}$;

$L^1$ is alkylene, arylene, —C(O)-alkylene, —C(O)-arylene, —C(O)O-arylene, —C(O)O— alkylene, —C(O)$NR^{20}$-alkylene, —C(O)$NR^{20}$-arylene, —C($NR^{20}$)$NR^{20}$-alkylene or —C($NR^{20}$)$NR^{20}$-arylene, wherein $L^1$ is configured such that —O-$L^1$-$R^{18}$ is —OC(O)-alkylene-$R^{18}$, —OC(O)O-arylene-$R^{18}$, —OC(O)O-alkylene-$R^{18}$, —OC(O)-arylene-$R^{18}$, —OC(O)$NR^{20}$-alkylene-$R^{18}$, —OC(O)$NR^{20}$-arylene-$R^{18}$, —OC($NR^{20}$)$NR^{20}$-alkylene-$R^{18}$ or —OC($NR^{20}$)$NR^{20}$-arylene-$R^{18}$, and wherein the alkylene and arylene are optionally substituted with 1 to 2 $R^{16}$;

$R^{13}$ is hydrogen, —$S(O)_2OR^{20}$, —$S(O)_2R^{20}$, —$C(O)R^{15}$, —$C(O)NR^{15}R^{15}$, —$C(O)OR^{15}$, $C_1$-$C_{12}$ alkyl optionally substituted with 1 to 5 $R^{16}$, $C_1$-$C_{12}$ alkenyl optionally substituted with 1 to 5 $R^{16}$, or aryl optionally substituted with 1 to 5 $R^{16}$;

$R^{14}$ is hydrogen, halo, —$OR^{17}$, —CN, $C_1$-$C_{12}$ alkyl, $C_1$-$C_{12}$ alkoxy, aryl or aryloxy, where the alkyl, alkoxy, aryl, and aryloxy are optionally substituted with 1 to 5 $R^{16}$;

each $R^{15}$ is independently selected from the group consisting of hydrogen, $C_1$-$C_{12}$ alkyl, $C_2$-$C_{12}$ alkenyl, $C_2$-$C_{12}$ alkynyl, aryl, heteroaryl, and heterocycle, and wherein the alkyl, alkenyl, alkynyl, aryl, heteroaryl, and heterocycle are optionally substituted with 1 to 5 $R^{16}$;

$R^{16}$ is selected from the group consisting of phenyl, halo, —$OR^{17}$, —CN, —$COR^{17}$, —$CO_2R^{17}$, —$NR^{17}R^{17}$, —$NR^{17}C(O)R^{17}$, —$NR^{17}SO_2R^{17}$, —$C(O)NR^{17}R^{17}$, —$C(O)NR^{17}NR^{17}R^{17}$, —$SO_2NR^{17}R^{17}$ and —$C(O)NR^{17}NR^{17}C(O)R^{17}$;

each $R^{17}$ is independently hydrogen or $C_1$-$C_{12}$ alkyl optionally substituted with from 1 to 3 halo;

$R^{18}$ is hydrogen, —$C(O)R^{20}$, —$C(O)OR^{20}$, —$C(O)N(R^{20})_2$ or —$N(R^{20})C(O)R^{20}$;

$R^{19}$ is hydrogen, —$N(R^{20})_2$, —$C(O)N(R^{20})_2$, —$C(NR^{20})N(R^{20})_2$, —$C(NSO_2R^{20})N(R^{20})_2$, —$NR^{20}C(O)N(R^{20})_2$, —$NR^{20}C(S)N(R^{20})_2$, —$NR^{20}C(NR^{20})N(R^{20})_2$, —$NR^{20}C(NSO_2R^{20})N(R^{20})_2$ or tetrazole; and each $R^{20}$ is independently selected from the group consisting of hydrogen, $C_1$-$C_{12}$ alkyl and aryl;

provided that:

when ===== is a double bond and $R^{13}$ and $R^{14}$ are hydrogen, then $R^{12}$ is not hydroxy;

when ===== is a double bond, $R^{14}$ is hydrogen, $R^{12}$ is —O-$L^1$-$R^{18}$, —O-$L^1$-$R^{19}$, —O-$L^1$-$R^{20}$, and $L^1$ is alkylene, then —O-$L^1$-$R^{18}$, —O-$L^1$-$R^{19}$, —O-$L^1$-$R^{20}$ are not methoxy;

when ===== is a double bond, $R^{14}$ is hydrogen, $R^z$ is O, $L^1$ is —C(O)-alkylene, —C(O)-arylene, —C(O)O-arylene, —C(O)O-alkylene, —C(O)$NR^{20}$-alkylene, or —C(O)$NR^{20}$-arylene, then none of $R^{18}$, $R^{19}$ or $R^{20}$ are hydrogen.

In one embodiment, the noribogaine derivative is represented by Formula IV:

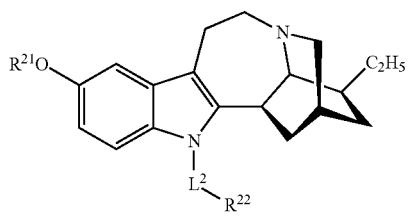

IV or a pharmaceutically acceptable salt thereof,
wherein $R^{21}$ is selected from the group consisting of hydrogen, a hydrolysable group selected from the group consisting of —$C(O)R^{23}$, —$C(O)NR^{24}R^{25}$ and —$C(O)OR^{26}$, where $R^{23}$ is selected from the group consisting of hydrogen, alkyl, substituted alkyl, alkenyl, substituted alkenyl, alkynyl and substituted alkynyl, $R^{24}$ and $R^{25}$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic, $R^{26}$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that $R^{21}$ is not a saccharide or an oligosaccharide;

$L^2$ is selected from the group consisting of a covalent bond and a cleavable linker group;

$R^{22}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, provided that R is not a saccharide or an oligosaccharide;

provided that when $L^2$ is a covalent bond and $R^{22}$ is hydrogen, then $R^{21}$ is selected from the group consisting of —C(O)NR$^{24}$R$^{25}$ and —C(O)OR$^{26}$; and further provided that when $R^{21}$ is hydrogen or —C(O)R$^{23}$ and $L^2$ is a covalent bond, then $R^{22}$ is not hydrogen.

In one embodiment, the noribogaine derivative is represented by Formula V:

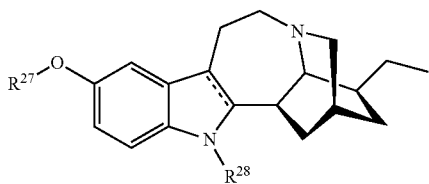

V or a pharmaceutically acceptable salt thereof, wherein:

⚍ refers to a single or a double bond provided that when ⚍ is a single bond, Formula V refers to the corresponding dihydro compound;

$R^{27}$ is hydrogen or SO$_2$OR$^{29}$;
$R^{28}$ is hydrogen or SO$_2$OR$^{29}$;
$R^{29}$ is hydrogen or C$_1$-C$_6$ alkyl;
provided that at least one of $R^{27}$ and $R^{28}$ is not hydrogen.

In one embodiment, the noribogaine derivative is represented by Formula VI:

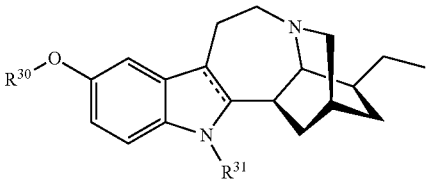

VI or a pharmaceutically acceptable salt thereof, wherein:

⚍ refers to a single or a double bond provided that when ⚍ is a single bond, Formula VI refers to the corresponding vicinal dihydro compound;

$R^{30}$ is hydrogen, a monophosphate, a diphosphate or a triphosphate; and $R^{31}$ is hydrogen, a monophosphate, a diphosphate or a triphosphate;

provided that both $R^{30}$ and $R^{31}$ are not hydrogen;

wherein one or more of the monophosphate, diphosphate and triphosphate groups of $R^{30}$ and $R^{31}$ are optionally esterified with one or more C$_1$-C$_6$ alkyl esters.

This invention is not limited to any particular chemical form of noribogaine, and the drug may be given to patients either as a free base or as a pharmaceutically acceptable acid addition salt. In the latter case, the hydrochloride salt is generally preferred, but other salts derived from organic or inorganic acids may also be used. Examples of such acids include, without limitation, those described below as "pharmaceutically acceptable salts" and the like. As discussed above, noribogaine itself may be formed from the O-demethylation of ibogaine which, in turn, may be synthesized by methods known in the art (see e.g., Huffman, et al., J. Org. Chem. 50:1460 (1985)).

"Pharmaceutically acceptable composition" refers to a composition that is suitable for administration to a mammal, particularly, a human. Such compositions include various excipients, diluents, carriers, and such other inactive agents well known to the skilled artisan.

"Pharmaceutically acceptable salt" refers to pharmaceutically acceptable salts, including pharmaceutically acceptable partial salts, of a compound, which salts are derived from a variety of organic and inorganic counter ions well known in the art and include, by way of example only, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, oxalic acid and the like, and when the molecule contains an acidic functionality, include, by way of example only, sodium, potassium, calcium, magnesium, ammonium, tetraalkylammonium, and the like.

A "pharmaceutically acceptable solvate" or "hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

As used herein the term "solvate" is taken to mean that a solid-form of a compound that crystallizes with one or more molecules of solvent trapped inside. A few examples of solvents that can be used to create solvates, such as pharmaceutically acceptable solvates, include, but are certainly not limited to, water, methanol, ethanol, isopropanol, butanol, C$_1$-C$_6$ alcohols in general (and optionally substituted), tetrahydrofuran, acetone, ethylene glycol, propylene glycol, acetic acid, formic acid, water, and solvent mixtures thereof. Other such biocompatible solvents which may aid in making a pharmaceutically acceptable solvate are well known in the art and applicable to the present invention. Additionally, various organic and inorganic acids and bases can be added or even used alone as the solvent to create a desired solvate. Such acids and bases are known in the art. When the solvent is water, the solvate can be referred to as a hydrate. Further, by being left in the atmosphere or recrystallized, the compounds of the present invention may absorb moisture, may include one or more molecules of water in the formed crystal, and thus become a hydrate. Even when such hydrates are formed, they are included in the term "solvate". Solvate also is meant to include such compositions where another compound or complex co-crystallizes with the compound of interest. The term "solvate" as used herein refers to complexes with solvents in which noribogaine is reacted or from which noribogaine is precipitated or crystallized. For example, a complex with water is known as a "hydrate". Solvates of noribogaine are within the scope of the invention. It will be appreciated by those skilled in organic chemistry that many organic compounds can exist in more than one crystalline form. For example, crystalline form may vary based on the solvate used. Thus, all crystalline forms of noribogaine or the pharmaceutically acceptable solvates thereof are within the scope of the present invention.

"Therapeutically effective amount" or "therapeutic amount" refers to an amount of a drug or an agent that, when administered to a patient suffering from a condition, will have the intended therapeutic effect, e.g., alleviation, amelioration, palliation or elimination of one or more manifestations of the condition in the patient. The therapeutically effective amount will vary depending upon the patient and the condition being treated, the weight and age of the subject, the severity of the condition, the salt, solvate, or derivative of the active drug portion chosen, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of an agent, in the context of treating migraines and/or symptoms thereof, refers to an amount of the agent that attenuates the migraines and/or symptoms thereof.

The therapeutically effective amount of the compound may be higher or lower, depending on the route of administration used. For example, when direct blood administration (e.g., sublingual, pulmonary and intranasal delivery) is used, a lower dose of the compound may be administered. In one aspect, a therapeutically effective amount of noribogaine or derivative is from about 50 ng to less than 100 μg per kg of body weight. Where other routes of administration are used, a higher dose of the compound may be administered. In one embodiment, the therapeutically effective amount of the compound is from greater than about 1 mg to about 8 mg per kg of body weight per day.

A "therapeutic level" of a drug is an amount of noribogaine or a noribogaine derivative that is sufficient to treat or prevent migraines and/or symptoms thereof but not high enough to pose any significant risk to the patient. Therapeutic levels of drugs can be determined by tests that measure the actual concentration of the compound in the blood of the patient. This concentration is referred to as the "serum concentration."

A "sub-therapeutic level" of noribogaine or pharmaceutical salt and/or solvate thereof that is less than the therapeutic level described above. For example, the sub-therapeutic level of noribogaine may be e.g., 80%, 70%, 60%, 50%, 40%, 30%, 20%, or 10% less than a therapeutically effective amount (e.g., 120 mg) of noribogaine, or any subvalue or subrange there between. Sub-therapeutic levels of noribogaine may coincide with "maintenance amounts" of noribogaine which are amounts, less than the therapeutically effective amount, that provide some attenuation and/or prevention of post-acute withdrawal syndrome in a patient. The maintenance amount of the compound is expected to be less than the therapeutically effective amount.

As defined herein, a "prophylactically effective amount" of a drug is an amount, typically less than the therapeutically effective amount, that provides prevention of migraines and/or symptoms thereof in a patient. The prophylactically effective amount of the compound is expected to be less than the therapeutically effective amount because the level of inhibition may not need to be as high in a patient who is not currently experiencing migraine. For example, a prophylactically effective amount is preferably 90%, 80%, 70%, 60%, 50%, 40%, 30%, 20%, or 10% less than a therapeutically effective amount.

As defined herein, a "maintenance amount" of a drug or an agent is an amount, typically less than the therapeutically effective amount that provides attenuation and/or prevention of syndrome disease or disorder or symptoms of a disease or disorder in a patient. The maintenance amount of the compound is expected to be less than the therapeutically effective amount because the level of inhibition does not need to be as high in a patient who is no longer physically manifests a disease or disorder or symptoms of a disease or disorder. For example, a maintenance amount is preferably 90%, 80%, 70%, 60%, 50%, 40%, 30%, 20%, or 10% less than a therapeutically effective amount, or any subvalue or subrange there between.

"Treatment", "treating", and "treat" are defined as acting upon a disease, disorder, or condition with an agent, such as noribogaine, to reduce or ameliorate harmful or any other undesired effects of the disease, disorder, or condition and/or its symptoms. "Treatment," as used herein, covers the treatment of a human patient, and includes: (a) reducing the risk of occurrence of the condition in a patient determined to be predisposed to the condition but not yet diagnosed as having the condition, (b) impeding the development of the condition, and/or (c) relieving the condition, i.e., causing regression of the condition and/or relieving one or more symptoms of the condition. "Treating" or "treatment of" a condition or patient refers to taking steps to obtain beneficial or desired results, including clinical results such as the reduction of symptoms. For purposes of this invention, beneficial or desired clinical results include, but are not limited to: treating or preventing migraines and/or symptoms thereof.

As used herein, the term "patient" refers to mammals and includes humans and non-human mammals. Preferably, the patient is a human.

As used herein, the term "QT interval" refers to the measure of the time between the start of the Q wave and the end of the T wave in the electrical cycle of the heart. Prolongation of the QT interval refers to an increase in the QT interval.

The term "dose" refers to a range of noribogaine, noribogaine derivative, or pharmaceutical salt or solvate thereof that provides a therapeutic serum level of noribogaine when given to a patient in need thereof. The dose is recited in a range, for example from about 20 mg to about 120 mg, and can be expressed either as milligrams or as mg/kg body weight. The attending clinician will select an appropriate dose from the range based on the patient's weight, age, degree of addiction, health, and other relevant factors, all of which are well within the skill of the art.

The term "unit dose" refers to a dose of drug that is given to the patient to provide therapeutic results, independent of the weight of the patient. In such an instance, the unit dose is sold in a standard form (e.g., 20 mg tablet). The unit dose may be administered as a single dose or a series of subdoses. In some embodiments, the unit dose provides a standardized level of drug to the patient, independent of weight of patient. Many medications are sold based on a dose that is therapeutic to all patients based on a therapeutic window. In such cases, it is not necessary to titrate the dosage amount based on the weight of the patient.

II. COMPOSITIONS

As will be apparent to the skilled artisan upon reading this disclosure, this invention provides compositions for treating or preventing migraines and/or symptoms thereof in a subject, comprising noribogaine, noribogaine derivatives, prodrugs of noribogaine, or pharmaceutically acceptable salts of each thereof. In a preferred embodiment, the composition further comprises at least one agent known to treat or prevent migraines and/or symptoms thereof.

Agents known to treat and/or prevent migraines and/or symptoms thereof include, without limitation, analgesics (e.g., non-steroidal anti-inflammatory drugs [NSAIDs], acetaminophen [including in combination with acetylsalicylic acid and caffeine], aspirin, diclofenac, ibuprofen, metoclopramide), triptans (e.g., sumatriptan, rizatriptan, naratriptan, zolmitriptan, eletriptan, almotriptan, frovatriptan, and avitriptan), ergotamines (e.g., ergotamine and dihydroergotamine), and dexamethasone. Dosing for these agents is well-known in the art and/or can be determined by a skilled clinician.

In one aspect, the invention provides a pharmaceutical composition comprising a therapeutically or prophylactically effective amount of noribogaine, a therapeutically or prophylactically effective amount of an agent known to treat or prevent migraines, and a pharmaceutically acceptable excipient, wherein the therapeutically or prophylactically effective amount of noribogaine is an amount that delivers an aggregate amount of noribogaine of about 50 ng to about 10 µg per kg body weight per day. In some aspects, the therapeutically or prophylactically effective amount of noribogaine is an amount that delivers an aggregate amount of noribogaine of about 1 mg to about 4 mg per kg body weight per day.

In some aspects, the composition is formulated for administration once per day. In some aspects, the composition is formulated for administration two or more times per day.

In some embodiments, the composition is formulated for oral, sublingual, intranasal, buccal, or intrapulmonary delivery. In some embodiments, the composition is formulated for oral, transdermal, internal, pulmonary, rectal, nasal, vaginal, lingual, intravenous, intraarterial, intramuscular, intraperitoneal, intracutaneous or subcutaneous delivery. Routes of administration are discussed in further detail below in the subsection titled "Dosages and Routes of Administration." In one embodiment, the therapeutically effective amount of the compound is from about 1 mg to about 4 mg per kg body weight per day. In another embodiment, the therapeutically effective amount of the compound is from about 1 mg to about 3 mg per kg body weight per day. In another embodiment, the therapeutically effective amount of the compound is from about 1 mg to about 2 mg per kg body weight per day. In another embodiment, the therapeutically effective amount of the compound is from about 1.3 mg to about 3 mg per kg body weight per day. In another embodiment, the therapeutically effective amount of the compound is from about 1.5 mg to about 3 mg per kg body weight per day. In another embodiment, the therapeutically effective amount of the compound is from about 1.3 mg to about 4 mg per kg body weight per day. In another embodiment, the therapeutically effective amount of the compound is from about 1.5 mg to about 4 mg per kg body weight per day. The ranges include both extremes as well as any subranges there between.

In one embodiment, the therapeutically effective amount of the compound is about 4 mg/kg body weight per day. In one embodiment, the therapeutically effective amount of the compound is about 3 mg/kg body weight per day. In another embodiment, the therapeutically effective amount of the compound is about 2 mg per kg body weight per day. In another embodiment, the therapeutically effective amount of the compound is about 1.7 mg per kg body weight per day. In another embodiment, the therapeutically effective amount of the compound is about 1.5 mg per kg body weight per day. In another embodiment, the therapeutically effective amount of the compound is about 1.2 mg per kg body weight per day. In another embodiment, the therapeutically effective amount of the compound is about 1 mg per kg body weight per day.

Compounds Utilized

In one embodiment, the noribogaine derivative is represented by Formula I:

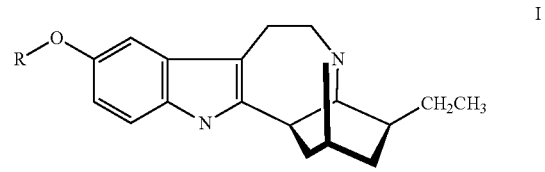

or a pharmaceutically acceptable salt and/or solvate thereof, wherein R is hydrogen or a hydrolyzable group such as hydrolyzable esters of from about 1 to 12 carbons.

Generally, in the above formula, R is hydrogen or a group of the formula:

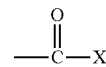

wherein X is a $C_1$-$C_{12}$ group, which is unsubstituted or substituted. For example, X may be a linear alkyl group such as methyl, ethyl, n-propyl, n-butyl, n-pentyl, n-hexyl, n-heptyl, n-octyl, n-nonyl, n-decyl, n-undecyl or n-dodecyl, or a branched alkyl group, such as i-propyl or sec-butyl. Also, X may be a phenyl group or benzyl group, either of which may be substituted with lower alkyl groups or lower alkoxy groups. Generally, the lower alkyl and/or alkoxy groups have from 1 to about 6 carbons. For example, the group R may be acetyl, propionyl or benzoyl. However, these groups are only exemplary.

Generally, for all groups X, they may either be unsubstituted or substituted with lower alkyl or lower alkoxy groups. For example, substituted X may be o-, m- or p-methyl or methoxy benzyl groups.

$C_1$-$C_{12}$ groups include $C_1$-$C_{12}$ alkyl, $C_3$-$C_{12}$ cycloalkyl, $C_6$-$C_{12}$ aryl, $C_7$-$C_{12}$ arylalkyl, wherein $C_x$ indicates that the group contains x carbon atoms. Lower alkyl refers to $C_1$-$C_4$ alkyl and lower alkoxy refers to $C_1$-$C_4$ alkoxy.

In one embodiment, the noribogaine derivative is represented by Formula II:

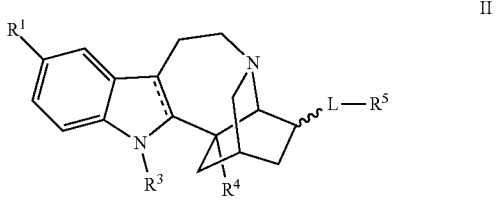

or a pharmaceutically acceptable salt and/or solvate thereof, wherein

===== is a single or double bond;

$R^1$ is halo, $OR^2$, or $C_1$-$C_{12}$ alkyl optionally substituted with 1 to 5 $R^{10}$;

$R^2$ is hydrogen or a hydrolysable group selected from the group consisting of —C(O)$R^x$, —C(O)O$R^x$ and —C(O)N($R^y$)$_2$ where each $R^x$ is selected from the group consisting of $C_1$-$C_6$ alkyl optionally substituted with 1 to 5 $R^{10}$, and each $R^y$ is independently selected from the group consisting of hydrogen, $C_1$-$C_6$ alkyl optionally substituted with 1 to 5 $R^{10}$, $C_6$-$C_{14}$ aryl optionally substituted with 1 to 5 $R^{10}$, $C_3$-$C_{10}$ cycloalkyl optionally substituted with 1 to 5 $R^{10}$, $C_1$-$C_{10}$ heteroaryl having 1 to 4 heteroatoms and which is optionally substituted with 1 to 5 $R^{10}$, $C_1$-$C_{10}$ heterocyclic having 1 to 4 heteroatoms and which is optionally substituted with 1 to 5 $R^{10}$, and where each $R^y$, together with the nitrogen atom bound thereto form a $C_1$-$C_6$ heterocyclic having 1 to 4 heteroatoms and which is optionally substituted with 1 to 5 $R^{10}$ or a $C_1$-$C_6$ heteroaryl having 1 to 4 heteroatoms and which is optionally substituted with 1 to 5 $R^{10}$;

$R^3$ is selected from the group consisting of hydrogen, $C_1$-$C_{12}$ alkyl optionally substituted with 1 to 5 $R^{10}$, aryl optionally substituted with 1 to 5 $R^{10}$, —C(O)$R^6$, —C(O)N$R^6R^6$ and —C(O)O$R^6$;

$R^4$ is selected from the group consisting of hydrogen, —(CH$_2$)$_m$O$R^8$, —C$R^7$(OH)$R^8$, —(CH$_2$)$_m$CN, —(CH$_2$)$_m$CO$R^8$, —(CH$_2$)$_m$CO$_2R^8$, —(CH$_2$)$_m$C(O)N$R^7R^8$, —(CH$_2$)$_m$C(O)N$R^7$N$R^8R^8$, —(CH$_2$)$_m$C(O)N$R^7$N$R^8$C(O)$R^9$, and —(CH$_2$)$_m$N$R^7R^8$;

m is 0, 1, or 2;

L is a bond or $C_1$-$C_{12}$ alkylene;

$R^5$ is selected from the group consisting of hydrogen, $C_1$-$C_{12}$ alkyl substituted with 1 to 5 $R^{10}$, $C_1$-$C_{12}$ alkenyl substituted with 1 to 5 $R^{10}$, —$X^1$—$R^7$, —($X^1$—Y)$_n$—$X^1$—$R^7$, —SO$_2$N$R^7R^8$, —O—C(O)$R^9$, —C(O)O$R^8$, —C(O)N$R^7R^8$, —N$R^7R^8$, —NHC(O)$R^9$, and —N$R^7$C(O)$R^9$;

each $R^6$ is independently selected from the group consisting of hydrogen, $C_1$-$C_{12}$ alkyl, $C_2$-$C_{12}$ alkenyl, $C_2$-$C_{12}$ alkynyl, $C_6$-$C_{10}$ aryl, $C_1$-$C_6$ heteroaryl having 1 to 4 heteroatoms, and $C_1$-$C_6$ heterocycle having 1 to 4 heteroatoms, and wherein the alkyl, alkenyl, alkynyl, aryl, heteroaryl, and heterocycle are optionally substituted with 1 to 5 $R^{10}$;

$X^1$ is selected from the group consisting of O and S;

Y is $C_1$-$C_4$ alkylene or $C_6$-$C_{10}$ arylene, or a combination thereof;

n is 1, 2, or 3;

$R^7$ and $R^8$ are each independently selected from the group consisting of hydrogen, $C_1$-$C_{12}$ alkyl optionally substituted with 1 to 5 $R^{10}$, $C_1$-$C_6$ heterocycle having 1 to 4 heteroatoms and which is optionally substituted with 1 to 5 $R^{10}$, $C_3$-$C_{10}$ cycloalkyl optionally substituted with 1 to 5 $R^{10}$, $C_6$-$C_{10}$ aryl optionally substituted with 1 to 5 $R^{10}$ and $C_1$-$C_6$ heteroaryl having 1 to 4 heteroatoms optionally substituted with 1 to 5 $R^{10}$;

$R^9$ is selected from the group consisting of $C_1$-$C_{12}$ alkyl optionally substituted with 1 to 5 $R^{10}$, $C_1$-$C_6$ heterocycle having 1 to 4 heteroatoms optionally substituted with 1 to 5 $R^{10}$, $C_3$-$C_{10}$ cycloalkyl optionally substituted with 1 to 5 $R^{10}$, $C_6$-$C_{10}$ aryl optionally substituted with 1 to 5 $R^{10}$ and $C_1$-$C_6$ heteroaryl having 1 to 4 heteroatoms optionally substituted with 1 to 5 $R^{10}$);

$R^{10}$ is selected from the group consisting of $C_1$-$C_4$ alkyl, phenyl, halo, —O$R^{11}$, —CN, —CO$R^{11}$, —CO$_2R^{11}$, —C(O)NH$R^{11}$, —N$R^{11}R^{11}$, —C(O)N$R^{11}R^{11}$, —C(O)NHN$R^{11}$, —C(O)N$R^{11}$NH$R^{11}$, —C(O)N$R^{11}R^{11}$, —C(O)NH$R^{11}$C(O)$R^{11}$, —C(O)NHNHC(O) $R^{11}$, —SO$_2$N$R^{11}R^{11}$, —C(O)N$R^{11}$N$R^{11}$C(O)$R^{11}$, and —C(O)N$R^{11}$NHC(O)$R^{11}$; and $R^{11}$ is independently hydrogen or $C_1$-$C_{12}$ alkyl;

provided that:

when L is a bond, then $R^5$ is not hydrogen;

when ===== is a double bond, $R^1$ is an ester hydrolyzable group, $R^3$ and $R^4$ are both hydrogen, then -L-$R^5$ is not ethyl;

when ===== is a double bond, $R^1$ is —OH, halo or $C_1$-$C_{12}$ alkyl optionally substituted with 1 to 5 $R^{10}$, then $R^4$ is hydrogen; and when ===== is a double bond, $R^1$ is O$R^2$, $R^4$ is hydrogen, -L-$R^5$ is ethyl, then $R^2$ is not a hydrolyzable group selected from the group consisting of an ester, amide, carbonate and carbamate.

In one embodiment, the noribogaine derivative is represented by Formula III:

or a pharmaceutically acceptable salt and/or solvate thereof, wherein

===== is a single or double bond;

$R^{12}$ is halo, —OH, —SH, —NH$_2$, —S(O)$_2$N($R^{17}$)$_2$, —$R^z$-$L^1$-$R^{18}$, —$R^z$-$L^1$-$R^{19}$, —$R^z$-$L^1$-$R^{20}$ or —$R^z$-$L^1$-CH$R^{18}R^{19}$, where $R^z$ is O, S or N$R^{17}$;

$L^1$ is alkylene, arylene, —C(O)-alkylene, —C(O)-arylene, —C(O)O-arylene, —C(O)O— alkylene, —C(O)N$R^{20}$-alkylene, —C(O)N$R^{20}$-arylene, —C(N$R^{20}$)N$R^{20}$-alkylene or —C(N$R^{20}$)N$R^{20}$-arylene, wherein $L^1$ is configured such that —O-$L^1$-$R^{18}$ is —OC(O)-alkylene-$R^{18}$, —OC(O)O-arylene-$R^{18}$, —OC(O)O-alkylene-$R^{18}$, —OC(O)-arylene-$R^{18}$, —OC(O)N$R^{20}$-alkylene-$R^{18}$, —OC(O)N$R^{20}$-arylene-$R^{18}$, —OC(N$R^{20}$)N$R^{20}$-alkylene-$R^{18}$ or —OC(N$R^{20}$)N$R^{20}$-arylene-$R^{18}$, and wherein the alkylene and arylene are optionally substituted with 1 to 2 $R^{16}$;

$R^{13}$ is hydrogen, —S(O)$_2$O$R^{20}$, —S(O)$_2R^{20}$, —C(O)$R^{15}$, —C(O)N$R^{15}R^{15}$, —C(O)O$R^{15}$, $C_1$-$C_{12}$ alkyl optionally substituted with 1 to 5 $R^{16}$, $C_1$-$C_{12}$ alkenyl optionally substituted with 1 to 5 $R^{16}$, or aryl optionally substituted with 1 to 5 $R^{16}$;

$R^{14}$ is hydrogen, halo, —O$R^{17}$, —CN, $C_1$-$C_{12}$ alkyl, $C_1$-$C_{12}$ alkoxy, aryl or aryloxy, where the alkyl, alkoxy, aryl, and aryloxy are optionally substituted with 1 to 5 $R^{16}$;

each $R^{15}$ is independently selected from the group consisting of hydrogen, $C_1$-$C_{12}$ alkyl, $C_2$-$C_{12}$ alkenyl, $C_2$-$C_{12}$ alkynyl, aryl, heteroaryl, and heterocycle, and wherein the alkyl, alkenyl, alkynyl, aryl, heteroaryl, and heterocycle are optionally substituted with 1 to 5 $R^{16}$;

$R^{16}$ is selected from the group consisting of phenyl, halo, —O$R^{17}$, —CN, —CO$R^{17}$, —CO$_2R^{17}$, —N$R^{17}R^{17}$, —N$R^{17}$C(O)$R^{17}$, —N$R^{17}$SO$_2R^{17}$, —C(O)N$R^{17}R^{17}$, —C(O)N$R^{17}$N$R^{17}R^{17}$, —SO$_2$N$R^{17}R^{17}$ and —C(O)N$R^{17}$N$R^{17}$C(O)$R^{17}$;

each $R^{17}$ is independently hydrogen or $C_1$-$C_{12}$ alkyl optionally substituted with from 1 to 3 halo;

$R^{18}$ is hydrogen, —C(O)$R^{20}$, —C(O)O$R^{20}$, —C(O)N($R^{20}$)$_2$ or —N($R^{20}$)C(O)$R^{20}$;

$R^{19}$ is hydrogen, —N($R^{20}$)$_2$, —C(O)N($R^{20}$)$_2$, —C(N$R^{20}$)N($R^{20}$)$_2$, —C(NSO$_2$$R^{20}$)N($R^{20}$)$_2$, —N$R^{20}$C(O)N($R^{20}$)$_2$, —N$R^{20}$C(S)N($R^{20}$)$_2$, —N$R^{20}$C(N$R^{20}$)N($R^{20}$)$_2$, —N$R^{20}$C(NSO$_2$$R^{20}$)N($R^{20}$)$_2$ or tetrazole; and each $R^{20}$ is independently selected from the group consisting of hydrogen, $C_1$-$C_{12}$ alkyl and aryl;

provided that:

when ===== is a double bond and $R^{13}$ and $R^{14}$ are hydrogen, then $R^{12}$ is not hydroxy;

when is ===== a double bond, $R^{14}$ is hydrogen, $R^{12}$ is —O-$L^1$-$R^{18}$, —O-$L^1$-$R^{19}$, —O-$L^1$-$R^{20}$, and $L^1$ is alkylene, then —O-$L^1$-$R^{18}$, —O-$L^1$-$R^{19}$, —O-$L^1$-$R^{20}$ are not methoxy;

when ===== is a double bond, $R^{14}$ is hydrogen, $R^z$ is O, $L^1$ is —C(O)-alkylene, —C(O)-arylene, —C(O)O-arylene, —C(O)O-alkylene, —C(O)N$R^{20}$-alkylene, or —C(O)N$R^{20}$-arylene, then none of $R^{18}$, $R^{19}$ or $R^{20}$ are hydrogen.

In one embodiment, the noribogaine derivative is represented by Formula IV:

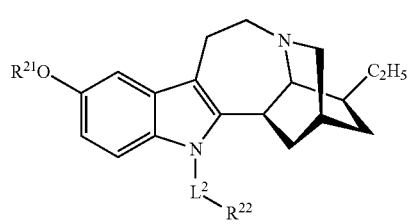

IV or a pharmaceutically acceptable salt and/or solvate thereof,
wherein
$R^{21}$ is selected from the group consisting of hydrogen, a hydrolysable group selected from the group consisting of —C(O)$R^{23}$, —C(O)N$R^{24}$$R^{25}$ and —C(O)O$R^{26}$, where $R^{23}$ is selected from the group consisting of hydrogen, alkyl, substituted alkyl, alkenyl, substituted alkenyl, alkynyl and substituted alkynyl, $R^{24}$ and $R^{25}$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic, $R^{26}$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that $R^{21}$ is not a saccharide or an oligosaccharide;

$L^2$ is selected from the group consisting of a covalent bond and a cleavable linker group;

$R^{22}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, provided that R is not a saccharide or an oligosaccharide;

provided that when $L^2$ is a covalent bond and $R^{22}$ is hydrogen, then $R^{21}$ is selected from the group consisting of —C(O)N$R^{24}$$R^{25}$ and —C(O)O$R^{26}$; and further provided that when $R^{21}$ is hydrogen or —C(O)$R^{23}$ and $L^2$ is a covalent bond, then $R^{22}$ is not hydrogen.

In one embodiment, the noribogaine derivative is represented by Formula V:

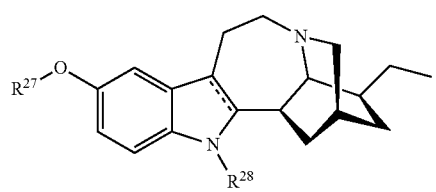

V or a pharmaceutically acceptable salt and/or solvate thereof, wherein:

===== refers to a single or a double bond provided that when ===== is a single bond, Formula V refers to the corresponding dihydro compound;

$R^{27}$ is hydrogen or SO$_2$O$R^{29}$;
$R^{28}$ is hydrogen or SO$_2$O$R^{29}$;
$R^{29}$ is hydrogen or $C_1$-$C_6$ alkyl;

provided that at least one of $R^{27}$ and $R^{28}$ is not hydrogen.

In one embodiment, the noribogaine derivative is represented by Formula VI:

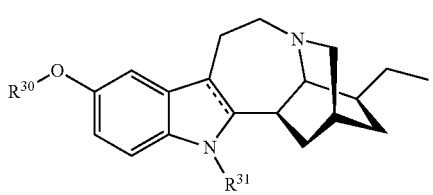

VI or a pharmaceutically acceptable salt and/or solvate thereof, wherein:

===== refers to a single or a double bond provided that when ===== is a single bond, Formula VI refers to the corresponding vicinal dihydro compound;

$R^{30}$ is hydrogen, a monophosphate, a diphosphate or a triphosphate; and $R^{31}$ is hydrogen, a monophosphate, a diphosphate or a triphosphate;

provided that both $R^{30}$ and $R^{31}$ are not hydrogen;
wherein one or more of the monophosphate, diphosphate and triphosphate groups of $R^{30}$ and $R^{31}$ are optionally esterified with one or more $C_1$-$C_6$ alkyl esters.

Noribogaine as utilized herein, can be replaced by a noribogaine derivative or a salt of noribogaine or the noribogaine derivative or a solvate of each of the foregoing.

In a preferred embodiment, the compound utilized herein is noribogaine or a salt thereof. In a more preferred embodiment, the compound utilized herein is noribogaine.

III. METHODS OF THE INVENTION

As will be apparent to the skilled artisan upon reading this disclosure, this invention, in one aspect, provides a method for treating or preventing migraines and/or symptoms thereof in a subject, comprising administering to the patient in need thereof a therapeutically effective amount of noribogaine, a noribogaine derivative, a noribogaine prodrug, or a pharmaceutically acceptable salt of each thereof. In one embodiment, the method further comprises administering at least one agent known to treat or prevent migraines and/or symptoms thereof.

a. Treating Migraine

In some embodiments, the invention provides for a method for treating migraines and/or symptoms thereof in a subject, comprising administering to the patient in need thereof a therapeutically effective amount of noribogaine, a noribogaine derivative, or a pharmaceutically acceptable salt of each thereof. In one embodiment, the method further comprises administering at least one agent known to treat or prevent migraines and/or symptoms thereof. In a preferred embodiment, treatment with noribogaine and/or the agent does not result in a QT interval prolongation of more than about 50 ms. Where noribogaine is discussed throughout the specification, it is to be understood that such an agent may optionally be administered in conjunction with (e.g., before, after, or concurrently with) noribogaine or derivative.

The subject or patient may be any patient who exhibits migraine and/or symptoms thereof. In a preferred embodiment, the patient is subject to recurrent migraines. In one embodiment, the patient has chronic migraine. Chronic migraine is characterized by headaches (tension and/or migraine) on more than 15 days per month for at least 3 months, with migraine (without aura) on at least 8 days per month (or successful treatment of expected symptoms).

In one aspect, this invention relates to a method for treating migraine and/or symptoms thereof in a patient, comprising administering to the patient a dosage of noribogaine, noribogaine derivative, or pharmaceutically acceptable salt or solvate thereof that provides an average serum concentration of about 50 ng/mL to about 180 ng/mL, said concentration being sufficient to treat said migraine and/or symptoms while maintaining a QT interval of less than about 500 ms during said treatment.

In some embodiments, the concentration is sufficient to treat the patient while maintaining a QT interval of less than about 470 ms during treatment. Preferably, the concentration is sufficient to treat the patient while maintaining a QT interval of less than about 450 ms during treatment. In one embodiment, the concentration is sufficient to treat the patient while maintaining a QT interval of less than about 420 ms during treatment.

In one embodiment, the QT interval is not prolonged more than about 50 ms. In one embodiment, the QT interval is not prolonged more than about 40 ms. In one embodiment, the QT interval is not prolonged more than about 30 ms. In one embodiment, the QT interval is not prolonged more than about 20 ms.

In one embodiment, the dosage of noribogaine, noribogaine derivative, or pharmaceutically acceptable salt or solvate thereof provides a serum concentration of between about 1000 ng·hr/mL and about 6000 ng·hr/mL (area under the curve for 24 hours, AUC/24 h). In one embodiment, the dosage of noribogaine, noribogaine derivative, or pharmaceutically acceptable salt or solvate thereof provides a serum concentration of between about 1200 ng·hr/mL and about 5800 ng·hr/mL (AUC/24 h). In one embodiment, the dosage of noribogaine, noribogaine derivative, or pharmaceutically acceptable salt or solvate thereof provides a serum concentration of between about 1200 ng·hr/mL and about 5500 ng·hr/mL (AUC/24 h). The ranges include both extremes as well as any subranges between.

In one embodiment, the dosage of noribogaine, noribogaine derivative, or pharmaceutically acceptable salt or solvate thereof provides a maximum serum concentration (Cmax) of less than about 250 ng/mL. In one embodiment, the dosage of noribogaine, noribogaine derivative, or pharmaceutically acceptable salt or solvate thereof provides a Cmax between about 40 ng/mL and about 250 ng/mL. In a preferred embodiment, the dosage of noribogaine, noribogaine derivative, or pharmaceutically acceptable salt or solvate thereof provides a Cmax between about 60 ng/mL and about 200 ng/mL. In one embodiment, the dosage of noribogaine, noribogaine derivative, or pharmaceutically acceptable salt or solvate thereof provides a Cmax between about 100 ng/mL and about 180 ng/mL.

In one embodiment, the dosage or aggregate dosage of noribogaine, noribogaine derivative, or salt or solvate thereof is from about 1 mg/kg to about 4 mg/kg body weight per day. The aggregate dosage is the combined dosage, for example the total amount of noribogaine, noribogaine derivative, or pharmaceutically acceptable salt or solvate thereof administered over a 24-hour period where smaller amounts are administered more than once per day. In one embodiment, the dosage or aggregate dosage of noribogaine, noribogaine derivative, or salt or solvate thereof is from about 1.3 mg/kg to about 4 mg/kg body weight. In one embodiment, the dosage or aggregate dosage of noribogaine, noribogaine derivative, or salt or solvate thereof is from about 1.3 mg/kg to about 3 mg/kg body weight. In one embodiment, the dosage or aggregate dosage of noribogaine, noribogaine derivative, or salt or solvate thereof is from about 1.3 mg/kg to about 2 mg/kg body weight. In one embodiment, the dosage or aggregate dosage of noribogaine, noribogaine derivative, or salt or solvate thereof is from about 1.5 mg/kg to about 3 mg/kg body weight. In one embodiment, the dosage or aggregate dosage of noribogaine, noribogaine derivative, or salt or solvate thereof is from about 1.7 mg/kg to about 3 mg/kg body weight. In one embodiment, the dosage or aggregate dosage of noribogaine, noribogaine derivative, or salt or solvate thereof is from about 2 mg/kg to about 4 mg/kg body weight. In one embodiment, the dosage or aggregate dosage of noribogaine, noribogaine derivative, or salt or solvate thereof is from about 2 mg/kg to about 3 mg/kg body weight. In one embodiment, the dosage or aggregate dosage of noribogaine, noribogaine derivative, or salt or solvate thereof is about 2 mg/kg body weight. The ranges include both extremes as well as any subranges there between.

In one embodiment, the dosage or aggregate dosage of noribogaine, noribogaine derivative, or salt or solvate thereof is between about 70 mg and about 150 mg. In one embodiment, the dosage or aggregate dosage of noribogaine, noribogaine derivative, or salt or solvate thereof is between about 75 mg and about 150 mg. In one embodiment, the dosage or aggregate dosage of noribogaine, noribogaine derivative, or salt or solvate thereof is between about 80 mg and about 140 mg. In one embodiment, the dosage or aggregate dosage of noribogaine, noribogaine derivative, or salt or solvate thereof is between about 90 mg and about 140 mg. In one embodiment, the dosage or aggregate dosage of noribogaine, noribogaine derivative, or salt or solvate thereof is between about 90 mg and about 130 mg. In one embodiment, the dosage or aggregate dosage of noribogaine, noribogaine derivative, or salt or solvate thereof is between about 100 mg and about 130 mg. In one embodiment, the dosage or aggregate dosage of noribogaine, noribogaine derivative, or salt or solvate thereof is between about 110 mg and about 130 mg.

In some embodiments, the therapeutically effective amount of the compound is from about 50 ng to about 10 µg per kilogram body weight per day. In another embodiment, the therapeutically effective amount of the compound is from about 50 ng to about 5 µg per kilogram body weight per day. In another embodiment, the therapeutically effective amount of the compound is from about 50 ng to about 1 µg per kilogram body weight per day. In another embodiment, the therapeutically effective amount of the compound is from about 50 ng to about 1 µg per kilogram body weight per day. In yet another embodiment, the therapeutically effective amount of the compound is from about 500 ng to less than 10 µg per kilogram body weight per day. In yet another embodiment, the therapeutically effective amount of the compound is from about 1 µg to less than 10 µg per kilogram body weight per day. In yet another embodiment, the therapeutically effective amount of the compound is about 50 ng, about 100 ng, about 150 ng, about 200 ng, about 250 ng, about 300 ng, about 350 ng, about 400 ng, about 450 ng, about 500 ng, about 550 ng, about 600 ng, about 650 ng, about 700 ng, about 750 ng, about 800 ng, about 850 ng, about 900 ng, about 950 ng, about 1 µg, about 2 µg, about 3 µg, about 3 µg, about 4 µg, about 5 µg, about 6 µg, about 7 µg, about 8 µg, about 9 µg, or about 10 µg per kilogram body weight per day. The therapeutically effective amount of the compound may be any amount within any of these ranges, including endpoints.

In some embodiments, the therapeutically effective amount of noribogaine, derivative, prodrug, or salt thereof is administered once a day. In some embodiments, the therapeutically effective amount is administered twice per day. In some embodiments, the therapeutically effective amount is administered more than two times per day.

Where the therapeutically effective amount is administered more than one time per day, a portion of the total therapeutically effective amount is administered at each time. For example, an 90 kg patient taking 1 µg noribogaine per kg body weight per day would take 90 µg once a day, 45 µg twice a day, or 30 µg three times a day, etc.

In some embodiments, the therapeutically effective amount of noribogaine, derivative, prodrug, or salt thereof is administered when needed, e.g., when the patient has a migraine or symptoms thereof or anticipates having a migraine (e.g., anticipates or experiences a trigger, has symptoms or predrome phase, etc).

In some embodiments, noribogaine, noribogaine derivative, or a pharmaceutically acceptable salt or solvate thereof is administered to a patient periodically, such as once, twice, three time, four times or five time daily. In some embodiments, the administration is once daily, or once every second day, once every third day, three times a week, twice a week, or once a week. The dosage and frequency of the administration depends on the route of administration, content of composition, age and body weight of the patient, condition of the patient, without limitation. Determination of dosage and frequency suitable for the present technology can be readily made by a qualified clinician.

In some embodiments, the noribogaine or noribogaine derivative is administered sublingually, intrapulmonary, buccally, or intranasally. These routes of administration are discussed in further detail below in the subsection titled "Dosages and Routes of Administration."

b. Preventing Migraine

In some embodiments, the invention provides for a method for preventing or attenuating migraine and/or symptoms thereof in a subject, comprising administering to the patient in need thereof a prophylactically effective amount of noribogaine, a noribogaine derivative, or a pharmaceutically acceptable salt of each thereof. In some embodiments, the invention provides for a method for preventing or attenuating migraine and/or symptoms thereof in a subject, comprising administering to the patient in need thereof a prophylactically effective amount of noribogaine, a noribogaine derivative, or a pharmaceutically acceptable salt of each thereof in conjunction with an agent known to prevent migraines and/or symptoms thereof. Where noribogaine is discussed throughout the specification, it is to be understood that such an agent may optionally be administered in conjunction with (e.g., before, after, concurrently or substantially concurrently with) noribogaine or derivative.

In some embodiments, the noribogaine is administered on an as-needed basis by the patient. In some embodiments, the noribogaine may be administered before the migraine and/or symptoms thereof occurs. For example, the patient may take a dose of noribogaine in anticipation of symptoms (e.g., after, concurrent with, or in anticipation of a migraine trigger; when one or more predrome symptoms are experienced; etc). In some embodiments, the prophylactically effective amount of noribogaine may be administered on a regularly scheduled basis (e.g., daily, every other day, weekly, etc.) to prevent migraine.

In one embodiment, the prophylactically effective amount of the compound is up to about 90% of the therapeutic amount. In one embodiment, the prophylactically effective amount of the compound is up to about 80% of the therapeutic amount. In one embodiment, the prophylactically effective amount of the compound is up to about 70% of the therapeutic amount. In one embodiment, the prophylactically effective amount of the compound is up to about 60% of the therapeutic amount. In one embodiment, the prophylactically effective amount of the compound is up to about 50% of the therapeutic amount. In one embodiment, the prophylactically effective amount of the compound is up to about 40% of the therapeutic amount. In one embodiment, the prophylactically effective amount of the compound is up to about 30% of the therapeutic amount. In one embodiment, the prophylactically effective amount of the compound is up to about 20% of the therapeutic amount. In one embodiment, the prophylactically effective amount of the compound is up to about 10% of the therapeutic amount.

In one embodiment, the prophylactically effective amount of the compound is from about 50 ng to less than 10 µg per kilogram body weight per day. In another embodiment, the prophylactically effective amount of the compound is from about 50 ng to about 5 µg per kilogram body weight per day. In another embodiment, the prophylactically effective amount of the compound is from about 50 ng to about 1 µg per kilogram body weight per day. In yet another embodiment, the prophylactically effective amount of the compound is from about 500 ng to less than 10 µg per kilogram body weight per day. In yet another embodiment, the prophylactically effective amount of the compound is from about 1 µg to less than 10 µg per kilogram body weight per day. The prophylactically effective amount of the compound may be any amount within any of these ranges, including endpoints.

In one embodiment, the QT interval is not prolonged more than about 30 ms. In a preferred embodiment, the QT interval is not prolonged more than about 20 ms.

In some embodiments, the prophylactically effective amount of noribogaine, derivative, prodrug, or salt thereof is administered once a day. In some embodiments, the prophylactically effective amount is administered twice per day. In some embodiments, the prophylactically effective amount is administered more than two times per day.

Where the prophylactically effective amount of noribogaine is administered more than one time per day, a portion of the total prophylactically effective amount is administered at each time. For example, an 90 kg patient taking 1 µg noribogaine per kg body weight per day would take 90 µg once a day, 45 µg twice a day, or 30 µg three times a day, etc.

In some embodiments, the patient is administered periodically, such as once, twice, three time, four times or five time daily with noribogaine, noribogaine derivative, or a pharmaceutically acceptable salt or solvate thereof. In some embodiments, the administration is once daily, or once every second day, once every third day, three times a week, twice a week, or once a week. The dosage and frequency of the administration depends on the route of administration, content of composition, age and body weight of the patient, condition of the patient, without limitation. Determination of dosage and frequency suitable for the present technology can be readily made a qualified clinician.

In some embodiments, the noribogaine or noribogaine derivative is administered orally, sublingually, intrapulmonary, buccally, or intranasally. These routes of administration are discussed in further detail below in the subsection titled "Dosages and Routes of Administration."

c. Dosages and Routes of Administration

The compositions, provided herein or known, suitable for administration in accordance with the methods provided herein, can be suitable for a variety of delivery modes including, without limitation, sublingual, buccal, intrapulmonary, or intranasal delivery. Compositions suitable for oral, internal, rectal, vaginal, lingual, intravenous, intraarterial, intramuscular, intraperitoneal, intracutaneous and subcutaneous routes may also be used. Other dosage forms include tablets, capsules, pills, powders, aerosols, suppositories, parenterals, and oral liquids, including suspensions, solutions and emulsions. Sustained release dosage forms may also be used. All dosage forms may be prepared using methods that are standard in the art (see e.g., Remington's Pharmaceutical Sciences, 16th ed., A. Oslo editor, Easton Pa. 1980).

In one embodiment, noribogaine, noribogaine derivative, or a pharmaceutically acceptable salt or solvate thereof is administered orally, which may conveniently be provided in tablet, caplet, sublingual, liquid or capsule form. In certain embodiments, the noribogaine is provided as noribogaine HCl, with dosages reported as the amount of free base noribogaine. In some embodiments, the noribogaine HCl is provided in hard gelatin capsules containing only noribogaine HCl with no excipients.

Noribogaine or a noribogaine derivative can also be used in conjunction with any of the vehicles and excipients commonly employed in pharmaceutical preparations, e.g., talc, gum Arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions containing noribogaine may be prepared using conventional techniques that may include sterile isotonic saline, water, 1,3-butanediol, ethanol, 1,2-propylene glycol, polyglycols mixed with water, Ringer's solution, etc.

The compositions utilized herein may be formulated for aerosol administration, particularly to the respiratory tract and including intrapulmonary or intranasal administration. The compound will generally have a small particle size, for example of the order of 5 microns or less. Such a particle size may be obtained by means known in the art, for example by micronization. The active ingredient may be provided in a pressurized pack with a suitable propellant such as a chlorofluorocarbon (CFC), (for example, dichlorodifluoromethane, trichlorofluoromethane, or dichlorotetrafluoroethane), carbon dioxide or other suitable gases. The aerosol may conveniently also contain a surfactant such as lecithin. The dose of drug may be controlled by a metered valve. Alternatively, the active ingredients may be provided in the form of a dry powder, for example a powder mix of the compound in a suitable powder base such as lactose, starch, starch derivatives such as hydroxypropylmethyl cellulose and polyvinylpyrrolidine. In some embodiments, the powder carrier will form a gel in the nasal cavity. The powder composition may be presented in unit dose form, for example in capsules or cartridges, gelatin or blister packs, from which the powder may be administered by means of an inhaler.

The compositions utilized herein may be formulated for sublingual administration, for example as sublingual tablets. Sublingual tablets are designed to dissolve very rapidly. The formulations of these tablets contain, in addition to the drug, a limited number of soluble excipients, usually lactose and powdered sucrose, but sometimes dextrose and mannitol.

It has been discovered that noribogaine has a bitter taste to at least some patients. Accordingly, compositions for oral use (including sublingual, inhaled, and other oral formulations) may be formulated to utilize taste-masking technologies. A number of ways to mask the taste of bitter drugs are known in the art, including addition of sugars, flavors, sweeteners, or coatings; use of lipoproteins, vesicles, and/or liposomes; granulation; microencapsulation; numbing of taste buds; multiple emulsion; modification of viscosity; prodrug or salt formation; inclusion or molecular complexes; ion exchange resins; and solid dispersion. Any method of masking the bitterness of the compound of the invention may be used.

In some embodiments, the patient is administered periodically, such as once, twice, three times, four times or five times daily with noribogaine, noribogaine derivative, or salt and/or solvate thereof. In some embodiments, the administration is once daily, or once every second day, once every third day, three times a week, twice a week, or once a week. The dosage and frequency of the administration depends on the route of administration, content of composition, age and body weight of the patient, condition of the patient, without limitation. Determination of dosage and frequency suitable for the present technology can be readily made by a qualified clinician.

In another embodiment, there is provided a unit dose of noribogaine, noribogaine derivative, or salt or solvate thereof which is about 50 mg to about 200 mg per dose. In one embodiment, the unit dose is about 50 to about 120 mg per dose. In one embodiment, the unit dose is about 120 mg per dose. It being understood that the term "unit dose" means a dose sufficient to provide therapeutic results whether given all at once or serially over a period of time.

Patient Pre-Screening and Monitoring

Pre-screening of patients before treatment with noribogaine and/or monitoring of patients during noribogaine, noribogaine derivative, or pharmaceutically acceptable sald and/or solvate thereof treatment may be required to ensure that QT interval is not prolonged beyond a certain value. For example, QT interval greater than about 500 ms can be considered dangerous for individual patients. Pre-screening and/or monitoring may be necessary at high levels of noribogaine treatment.

In a preferred embodiment, a patient receiving a therapeutic dose of noribogaine is monitored in a clinical setting. Monitoring may be necessary to ensure the QT interval is not prolonged to an unacceptable degree. A "clinical setting" refers to an inpatient setting (e.g., inpatient clinic, hospital, rehabilitation facility) or an outpatient setting with frequent, regular monitoring (e.g., outpatient clinic that is visited daily to receive dose and monitoring). Monitoring includes monitoring of QT interval. Methods for monitoring of QT interval are well-known in the art, for example by ECG.

In one embodiment, a patient receiving a maintenance dose of noribogaine is not monitored in a clinical setting. In one embodiment, a patient receiving a maintenance dose of noribogaine is monitored periodically, for example daily, weekly, monthly, or occasionally.

In one aspect, this invention relates to a method for treating, preventing, or attenuating a disease or disorder or symptoms of a disease or disorder described herein who is prescreened to evaluate the patient's expected tolerance for prolongation of QT interval, administering to the patient a dosage of noribogaine, noribogaine derivative, or pharmaceutically acceptable salt or solvate thereof that provides an average serum concentration of about 50 ng/mL to about 180 ng/mL, said concentration being sufficient to inhibit or ameliorate said abuse or symptoms while maintaining a QT interval of less than about 500 ms during said treatment. In some embodiments, the concentration is sufficient to attenuate said abuse or symptoms while maintaining a QT interval of less than about 470 ms during treatment. Preferably, the concentration is sufficient to attenuate said abuse or symptoms while maintaining a QT interval of less than about 450 ms during treatment. In one embodiment, the concentration is sufficient to attenuate said abuse or symptoms while maintaining a QT interval of less than about 420 ms during treatment.

In one embodiment, prescreening of the patient comprises ascertaining that noribogaine treatment will not result in a maximum QT interval over about 500 ms. In one embodiment, prescreening of the patient comprises ascertaining that noribogaine treatment will not result in a maximum QT interval over about 470 ms. In one embodiment, prescreening comprises ascertaining that noribogaine treatment will not result in a maximum QT interval over about 450 ms. In one embodiment, prescreening comprises ascertaining that noribogaine treatment will not result in a maximum QT interval over about 420 ms. In one embodiment, prescreening comprises determining the patient's pre-treatment QT interval.

As it relates to pre-screening or pre-selection of patients, patients may be selected based on any criteria as determined by the skilled clinician. Such criteria may include, by way of non-limiting example, pre-treatment QT interval, pre-existing cardiac conditions, risk of cardiac conditions, age, sex, general health, and the like. The following are examples of selection criteria for disallowing noribogaine treatment or restricting dose of noribogaine administered to the patient: high QT interval before treatment (e.g., such that there is a risk of the patient's QT interval exceeding about 500 ms during treatment); congenital long QT syndrome; bradycardia; hypokalemia or hypomagnesemia; recent acute myocardial infarction; uncompensated heart failure; and taking other drugs that increase QT interval. In some embodiments, the methods can include selecting and/or administering/providing noribogaine to a patient that lacks one more of such criteria.

In one embodiment, this invention relates to pre-screening a patient to determine if the patient is at risk for prolongation of the QT interval beyond a safe level. In one embodiment, a patient at risk for prolongation of the QT interval beyond a safe level is not administered noribogaine. In one embodiment, a patient at risk for prolongation of the QT interval beyond a safe level is administered noribogaine at a limited dosage.

In one embodiment, this invention relates to monitoring a patient who is administered a therapeutic dose of noribogaine. In one embodiment, the dose of noribogaine is reduced if the patient has serious adverse side effects. In one embodiment, the noribogaine treatment is discontinued if the patient has serious adverse side effects. In one embodiment, the adverse side effect is a QT interval that is prolonged beyond a safe level. The determination of a safe level of prolongation is within the skill of a qualified clinician.

Kit of Parts

One aspect of this invention is directed to a kit of parts for the treatment, prevention, or attenuation of a disease or disorder or symptoms of a disease or disorder described herein, wherein the kit comprises a composition comprising noribogaine, noribogaine derivative, or salt or solvate thereof and a means for administering the composition to a patient in need thereof. The means for administration to a patient can include, for example, any one or combination of a pharmaceutically acceptable formulation comprising noribogaine, or a noribogaine derivative, or a pharmaceutically acceptable salt or solvate thereof (e.g., a pill, transdermal patch, injectable, and the like, without limitation) and optionally a means for dispensing and/or administering the formulation (e.g., a syringe, a needle, an IV bag comprising the composition, a vial comprising the composition, an inhaler comprising the composition, etc, without limitation). In one embodiment, the kit of parts further comprises instructions for dosing and/or administration of the composition.

In some aspects, the invention is directed to a kit of parts for administration of noribogaine, the kit comprising multiple delivery vehicles, wherein each delivery vehicle contains a discrete amount of noribogaine and further wherein each delivery vehicle is identified by the amount of noribogaine provided therein; and optionally further comprising a dosing treatment schedule in a readable medium. In some embodiments, the dosing treatment schedule includes the amount of noribogaine required to achieve each average serum level is provided. In some embodiments, the kit of parts includes a dosing treatment schedule that provides an attending clinician the ability to select a dosing regimen of noribogaine based on the sex of the patient, mass of the patient, and the serum level that the clinician desires to achieve. In some embodiments, the dosing treatment schedule further provides information corresponding to the volume of blood in a patient based upon weight (or mass) and sex of the patient. In an embodiment, the storage medium can include an accompanying pamphlet or similar written information that accompanies the unit dose form in the kit. In an embodiment, the storage medium can include electronic, optical, or other data storage, such as a non-volatile memory, for example, to store a digitally-encoded machine-readable representation of such information.

The term "delivery vehicle" as used herein refers to any formulation that can be used for administration of noribogaine to a patient. Non-limiting, exemplary delivery vehicles include caplets, pills, capsules, tablets, powder, liquid, or any other form by which the drug can be administered. Delivery vehicles may be intended for administration by oral, inhaled, injected, or any other means.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

In some aspects, the machine-readable medium comprises software that contains information regarding dosing schedules for the unit dose form of noribogaine and optionally other drug information. In some embodiments, the software may be interactive, such that the attending clinician or other medical professional can enter patient information. In a non-limiting example, the medical professional may enter the weight and sex of the patient to be treated, and the software program provides a recommended dosing regimen based on the information entered. The amount and timing of noribogaine recommended to be delivered will be within the dosages that result in the serum concentrations as provided herein.

In some embodiments, the kit of parts comprises multiple delivery vehicles in a variety of dosing options. For example, the kit of parts may comprise pills or tablets in multiple dosages, such as 120 mg, 90 mg, 60 mg, 30 mg, 20 mg, 10 mg, and/or 5 mg of noribogaine per pill. Each pill is labeled such that the medical professional and/or patient can easily distinguish different dosages. Labeling may be based on printing or embossing on the pill, shape of the pill, color of pill, the location of the pill in a separate, labeled compartment within the kit, and/or any other distinguishing features of the pill. In some embodiments, all of the delivery vehicles within a kit are intended for one patient. In some embodiments, the delivery vehicles within a kit are intended for multiple patients.

One aspect of this invention is directed to a kit of parts for the treatment, prevention, or attenuation of a disease or disorder or symptoms of a disease or disorder described herein, wherein the kit comprises a unit dose form of noribogaine, noribogaine derivative, or salt or solvate thereof. The unit dose form provides a patient with an average serum level of noribogaine of from about 50 ng/mL to about 180 ng/mL or about 60 ng/mL to about 180 ng/mL. The unit dose form provides a patient with an average serum level of noribogaine of from about 50 ng/mL to about 800 ng/mL or about 60 ng/mL to about 800 ng/mL. In one embodiment, the unit dose form provides a patient with an average serum level of noribogaine of from about 50 ng/mL to about 400 ng/mL or about 60 ng/mL to about 400 ng/mL. In one embodiment, the unit dose form provides a patient with an average serum level of noribogaine of from 80 ng/mL to 100 ng/mL.

In some embodiments, the unit dose of noribogaine, noribogaine derivative, or pharmaceutically acceptable salt or solvate thereof is from 20 mg to 120 mg. In one embodiment, the unit dose is 20 mg. In one embodiment, the unit dose is 30 mg. In one embodiment, the unit dose is 40 mg. In one embodiment, the unit dose is 50 mg. In one embodiment, the unit dose is 60 mg. In one embodiment, the unit dose is 70 mg. In one embodiment, the unit dose is 80 mg. In one embodiment, the unit dose is 90 mg. In one embodiment, the unit dose is 100 mg. In one embodiment, the unit dose is 110 mg. In one embodiment, the unit dose is 120 mg.

In some embodiments, the unit dose form comprises one or multiple dosages to be administered periodically, such as once, twice, three times, four times or five times daily with noribogaine or its prodrug. In some embodiments, the administration is once daily, or once every second day, once every third day, three times a week, twice a week, or once a week. The dosage and frequency of the administration depends on criteria including the route of administration, content of composition, age and body weight of the patient, condition of the patient, sex of the patient, without limitation, as well as by the severity of the addiction. Determination of the unit dose form providing a dosage and frequency suitable for a given patient can readily be made by a qualified clinician.

In some embodiments, the initial unit dose and one or more additional doses of noribogaine, noribogaine derivative, or salt or solvate thereof are provided as one or multiple dosages to be administered periodically, such as once, twice, three times, four times or five times daily with noribogaine or its prodrug. In some embodiments, the administration is once daily, or once every second day, once every third day, three times a week, twice a week, or once a week. The dosage and frequency of the administration depends on criteria including the route of administration, content of composition, age and body weight of the patient, condition of the patient, sex of the patient, without limitation, as well as by the severity of the addiction. Determination of the unit dose form providing a dosage and frequency suitable for a given patient can readily be made by a qualified clinician.

In one aspect, provided herein is a kit of parts comprising two or more doses of noribogaine, noribogaine derivative, or pharmaceutically acceptable salt or solvate thereof, wherein the two or more doses comprise an amount of noribogaine, noribogaine derivative, or pharmaceutically acceptable salt or solvate thereof that is sufficient to maintain a serum concentration of 50 ng/mL to 180 ng/mL when administered to a patient.

In one embodiment, one dose comprises an initial dose of noribogaine, noribogaine derivative, or pharmaceutically acceptable salt or solvate thereof, said initial dose being sufficient to achieve a therapeutic serum concentration when administered to a patient; and
at least one additional dose, said additional dose sufficient to maintain a therapeutic serum concentration when administered to a patient, wherein the therapeutic serum concentration is between 50 ng/mL and 180 ng/mL In another embodiment, the initial dose is from 75 mg to 120 mg. In another embodiment, the at least one additional dose is from 5 mg to 25 mg.

These dose ranges may be achieved by transdermal, oral, or parenteral administration of noribogaine, noribogaine derivative, or a pharmaceutically acceptable salt or solvate thereof in unit dose form. Such unit dose form may conveniently be provided in transdermal patch, tablet, caplet, liquid or capsule form. In certain embodiments, the noribogaine is provided as noribogaine HCl, with dosages reported as the amount of free base noribogaine. In some embodiments, the noribogaine HCl is provided in hard gelatin capsules containing only noribogaine HCl with no excipients. In some embodiments, noribogaine is provided in saline for intravenous administration.

Formulations

This invention further relates to pharmaceutically acceptable formulations comprising a unit dose of noribogaine, noribogaine derivative, or pharmaceutically acceptable salt or solvate thereof, wherein the amount of noribogaine is sufficient to provide an average serum concentration of about 50 ng/mL to about 180 ng/mL when administered to a patient. In a preferred embodiment, the amount of noribogaine is sufficient to provide an average serum concentration of about 80 ng/mL to about 100 ng/mL when administered to a patient. In one embodiment, the amount of noribogaine, noribogaine derivative, or pharmaceutically acceptable salt thereof is an amount that delivers an aggregate amount of noribogaine of about 50 ng to about 10 μg per kg body weight per day.

In some embodiments, the unit dose of noribogaine is administered in one or more dosings.

This invention further relates to pharmaceutically acceptable formulations comprising a unit dose of noribogaine, noribogaine derivative, or pharmaceutically acceptable salt or solvate thereof, wherein the amount of noribogaine is sufficient to provide and/or maintain an average serum concentration of about 50 ng/mL to about 180 ng/mL when administered to a patient. In a preferred embodiment, the amount of noribogaine is sufficient to provide and/or maintain an average serum concentration of 80 ng/mL to 100 ng/mL when administered to a patient.

In some embodiments, the unit dose of noribogaine is administered in one or more dosings.

In one embodiment, the amount of noribogaine is sufficient to provide an average serum concentration of noribogaine from 50 ng/mL to 180 ng/mL, or 60 ng/mL to 180 ng/mL. In one embodiment, the amount of noribogaine is sufficient to provide an average serum concentration of noribogaine from 50 ng/mL to 150 ng/mL, or 60 ng/mL to 150 ng/mL. In one embodiment, the amount of noribogaine is sufficient to provide an average serum concentration of noribogaine from about 50 ng/mL to about 120 ng/mL, or about 60 ng/mL to about 120 ng/mL. In one embodiment, the amount of noribogaine is sufficient to provide an average serum concentration of noribogaine from about 50 ng/mL to about 100 ng/mL, or about 60 ng/mL to about 100 ng/mL. In one embodiment, the amount of noribogaine is sufficient to provide an average serum concentration of noribogaine from about 50 ng/mL to about 120 ng/mL, or about 60 ng/mL to about 120 ng/mL. In one embodiment, the amount of noribogaine is sufficient to provide an average serum concentration of noribogaine from about 50 ng/mL to about 100 ng/mL, or about 60 ng/mL to about 100 ng/mL. In one embodiment, the amount of noribogaine is sufficient to provide an average serum concentration of noribogaine from about 80 ng/mL to about 100 ng/mL. The ranges include both extremes as well as any subranges between.

In some embodiments, the initial unit dose of noribogaine, noribogaine derivative, or pharmaceutically acceptable salt or solvate thereof is from about 50 mg to about 120 mg. In one embodiment, the unit dose is about 50 mg. In one embodiment, the unit dose is about 55 mg. In one embodiment, the unit dose is 60 mg. In one embodiment, the unit dose is about 65 mg. In one embodiment, the unit dose is about 70 mg. In one embodiment, the unit dose is about 75 mg. In one embodiment, the unit dose is about 80 mg. In one embodiment, the unit dose is about 85 mg. In one embodiment, the unit dose is about 90 mg. In one embodiment, the unit dose is about 95 mg. In one embodiment, the unit dose is about 100 mg. In embodiment, the unit dose is 105 mg. In one embodiment, the unit dose is about 110 mg. In one embodiment, the unit dose is about 115 mg. In one embodiment, the unit dose is about 120 mg.

In some embodiments, the at least one additional dose of noribogaine, noribogaine derivative, or pharmaceutically acceptable salt or solvate thereof is from 5 mg to 75 mg. In one embodiment, the unit dose is 5 mg. In one embodiment, the unit dose is 10 mg. In one embodiment, the unit dose is 15 mg. In one embodiment, the unit dose is 20 mg. In one embodiment, the unit dose is 25 mg. In one embodiment, the unit dose is 30 mg. In one embodiment, the unit dose is 35 mg. In one embodiment, the unit dose is 40 mg. In one embodiment, the unit dose is 45 mg. In one embodiment, the unit dose is 50 mg. In one embodiment, the unit dose is 55 mg. In one embodiment, the unit dose is 60 mg. In one embodiment, the unit dose is 65 mg. In one embodiment, the unit dose is 70 mg. In one embodiment, the unit dose is 75 mg.

In some embodiments, the formulation comprises a delivery vehicle, as described above. In one embodiment, the delivery vehicle comprises 5 mg to 120 mg noribogaine, noribogaine derivative, or pharmaceutically acceptable salt or solvate thereof.

In some embodiments, the formulation is a controlled release formulation. The term "controlled release formulation" includes sustained release and time-release formulations. Controlled release formulations are well-known in the art. These include excipients that allow for sustained, periodic, pulse, or delayed release of the drug. Controlled release formulations include, without limitation, embedding of the drug into a matrix; enteric coatings; microencapsulation; gels and hydrogels; implants; transdermal patches; and any other formulation that allows for controlled release of a drug.

In one embodiment, the amount of noribogaine is sufficient to provide an average serum concentration of noribogaine from about 50 ng/mL to about 180 ng/mL, or about 60 ng/mL to about 180 ng/mL. In one embodiment, the amount of noribogaine is sufficient to provide an average serum concentration of noribogaine from about 50 ng/mL to about 150 ng/mL, or about 60 ng/mL to about 150 ng/mL. In one embodiment, the amount of noribogaine is sufficient to provide an average serum concentration of noribogaine from about 50 ng/mL to about 120 ng/mL, or about 60 ng/mL to about 120 ng/mL. In one embodiment, the amount of noribogaine is sufficient to provide an average serum concentration of noribogaine from about 50 ng/mL to about 100 ng/mL, or about 60 ng/mL to about 100 ng/mL. In one embodiment, the amount of noribogaine is sufficient to provide an average serum concentration of noribogaine from about 80 ng/mL to about 100 ng/mL. The ranges include both extremes as well as any subranges between.

In some embodiments, the unit dose of noribogaine, noribogaine derivative, or pharmaceutically acceptable salt or solvate thereof is from about 20 mg to about 120 mg. In one embodiment, the unit dose is about 20 mg. In one embodiment, the unit dose is about 30 mg. In one embodiment, the unit dose is about 40 mg. In one embodiment, the unit dose is about 50 mg. In one embodiment, the unit dose is about 60 mg. In one embodiment, the unit dose is about 70 mg. In one embodiment, the unit dose is about 80 mg. In one embodiment, the unit dose is about 90 mg. In one embodiment, the unit dose is about 100 mg. In one embodiment, the unit dose is about 110 mg. In one embodiment, the unit dose is about 120 mg.

This invention further relates to pharmaceutically acceptable formulations comprising a unit dose of noribogaine, noribogaine derivative, or pharmaceutically acceptable salt and/or solvate thereof, wherein the amount of noribogaine is sufficient to provide an average serum concentration of about 50 ng/mL to about 850 ng/mL when administered to a patient. In a preferred embodiment, the amount of noribogaine is sufficient to provide an average serum concentration of about 50 ng/mL to about 400 ng/mL when administered to a patient.

In one embodiment, the amount of noribogaine is sufficient to provide an average serum concentration of noribogaine from about 50 ng/mL to about 800 ng/mL or about 60 ng/mL to about 800 ng/mL. In one embodiment, the amount of noribogaine is sufficient to provide an average serum concentration of noribogaine from about 50 ng/mL to about 700 ng/mL or about 60 ng/mL to about 700 ng/mL. In one embodiment, the amount of noribogaine is sufficient to provide an average serum concentration of noribogaine from about 50 ng/mL to about 600 ng/mL, or about 60 ng/mL to about 600 ng/mL. In a preferred embodiment, the amount of noribogaine is sufficient to provide an average serum concentration of noribogaine from about 50 ng/mL to about 500 ng/mL, or about 60 ng/mL to about 500 ng/mL. In one embodiment, the amount of noribogaine is sufficient to provide an average serum concentration of noribogaine from about 50 ng/mL to about 400 ng/mL, or about 60 ng/mL to about 400 ng/mL. In one embodiment, the amount of noribogaine is sufficient to provide an average serum concentration of noribogaine from about 50 ng/mL to about 300 ng/mL, or about 60 ng/mL to about 300 ng/mL. In one embodiment, the amount of noribogaine is sufficient to provide an average serum concentration of noribogaine from about 50 ng/mL to about 200 ng/mL, or about 60 ng/mL to about 200 ng/mL. In one embodiment, the amount of noribogaine is sufficient to provide an average serum concentration of noribogaine from about 50 ng/mL to about 100 ng/mL, or about 60 ng/mL to about 100 ng/mL. The ranges include both extremes as well as any subranges between.

In some embodiments, the formulation is designed for periodic administration, such as once, twice, three times, four times or five times daily with noribogaine, noribogaine derivative, or a pharmaceutically acceptable salt or solvate thereof. In some embodiments, the administration is once daily, or once every second day, once every third day, three times a week, twice a week, or once a week. The dosage and frequency of the administration depends on the route of administration, content of composition, age and body weight of the patient, condition of the patient, without limitation. Determination of dosage and frequency suitable for the present technology can be readily made a qualified clinician.

In some embodiments, the formulation designed for administration in accordance with the methods provide herein can be suitable for a variety of delivery modes including, without limitation, oral, transdermal, sublingual, buccal, intrapulmonary or intranasal delivery. Formulations suitable for internal, pulmonary, rectal, nasal, vaginal, lingual, intravenous, intra-arterial, intramuscular, intraperitoneal, intracutaneous and subcutaneous routes may also be used. Possible formulations include tablets, capsules, pills, powders, aerosols, suppositories, parenterals, and oral liquids, including suspensions, solutions and emulsions. Sustained release dosage forms may also be used. All formulations may be prepared using methods that are standard in the art (see e.g., Remington's Pharmaceutical Sciences, 16th ed., A. Oslo editor, Easton Pa. 1980).

In a preferred embodiment, the formulation is designed for oral administration, which may conveniently be provided in tablet, caplet, sublingual, liquid or capsule form. In certain embodiments, the noribogaine is provided as noribogaine HCl, with dosages reported as the amount of free base noribogaine. In some embodiments, the noribogaine HCl is provided in hard gelatin capsules containing only noribogaine HCl with no excipients.

EXAMPLES

Additional embodiments are disclosed in further detail in the following examples, which are not in any way intended to limit the scope of the claims.

Example 1

Pharmacokinetics and Pharmacodynamics of Noribogaine in Humans

Thirty-six healthy, drug-free male volunteers, aged between 18-55 years, were enrolled in and completed the study. This was an ascending single-dose, placebo-controlled, randomized double blind, parallel group study. Mean (SD) age was 22.0 (3.3) years, mean (SD) height was 1.82 (0.08) m, and mean (SD) weight was 78.0 (9.2) kg. Twenty-six subjects were Caucasian, 3 were Asian, 1 Maori, 1 Pacific Islander, and 5 Other. The protocol for this study was approved by the Lower South Regional Ethics Committee (LRS/12/06/015), and the study was registered with the Australian New Zealand Clinical Trial Registry (AC-TRN12612000821897). All subjects provided signed informed consent prior to enrolment, and were assessed as suitable to participate based on review of medical history, physical examination, safety laboratory tests, vital signs and ECG.

Within each dose level, 6 participants were randomized to receive noribogaine and 3 to receive placebo, based on a computer-generated random code. Dosing began with the lowest noribogaine dose, and subsequent cohorts received the next highest dose after the safety, tolerability, and blinded pharmacokinetics of the completed cohort were reviewed and dose-escalation approved by an independent Data Safety Monitoring Board. Blinded study drug was administered as a capsule with 240 ml of water after an overnight fast of at least 10 hours. Participants did not receive any food until at least 5 hours post-dose. Participants were confined to the study site from 12 hours prior to drug administration, until 72 hours post-dose, and there were subsequent outpatient assessments until 216 hours post-dose.

Blood was obtained for pharmacokinetic assessments pre-dose and then at 0.25, 0.5, 0.75, 1.0, 1.25, 1.5, 2, 2.5, 3, 3.5, 4, 4.5, 5, 5.5, 6, 7, 8, 10, 12, 14, 18, 24, 30, 36, 48, 60, 72, 96, 120, 168 and 216 hours post-dose. Samples were centrifuged and plasma stored at −70° C. until analyzed. Block 24 hour urine collections were obtained following study drug administration for the 30 and 60 mg cohorts. Aliquots were frozen at −20° C. until analyzed.

Pulse oximetry and capnography data were collected continuously using a GE Carescape B650 monitoring system from 2 hours prior to dosing and until six hours after dosing, and thereafter at 12, 24, 48 and 72 hours post-dosing. Additional oximetry data were collected at 120, 168 and 216 hours. Pupillary miosis was assessed by pupillometry. Dark-adapted pupil diameter was measured in triplicate using a Neuroptics PLR-200 pupillometer under standardized light intensity (<5 lux) pre-dose, and at 2, 4, 6, 12, 24, 48, 72, 96, 120, 168 and 216 hours post-dosing.

Plasma noribogaine concentrations were determined in the 3 mg and 10 mg dose groups using a validated, sensitive LCMSMS method. Sample preparation involved double extraction of basified plasma samples with tert-butyl methyl ether, drying the samples under a stream of nitrogen and reconstitution of sample with acetonitrile:B.P. water (5:95, v/v) containing 0.1% (v/v) formic acid. The compounds were separated by a 150×2.0 mm Luna 5 µm C18 column and detected with a triple-quadrupole API 4000 or 5000 mass spectrometer using electrospray ionization in positive mode and multiple reaction monitoring. Noribogaine-$d_4$ was used as the internal standard. The precursor-product ion transition values for noribogaine were m/z 297.6→122.3, and for the internal standard noribogaine-$d_4$ m/z 301.1→122.2. Analyst® software was used for data acquisition and processing. The ratio of the peak area of noribogaine to the internal standard noribogaine-$d_4$ was used for calibration and measurement of the unknown concentration of noribogaine. The lower limit of quantification (LLOQ) was 0.025 ng/ml noribogaine. The calibration curve was between 0.025 and 25.600 ng/ml noribogaine. Mobile phase A was acetonitrile:B.P. water (5:95, v/v) containing 0.1% (v/v) formic acid, and mobile phase B was acetonitrile:B.P. water (95:5, v/v) containing 0.1% (v/v) formic acid. Total run time was 6 minutes. Binary flow: Initial concentration was 8% mobile phase B; hold at 8% mobile phase B for 0.5 minutes and linear rise to 90% mobile phase B over 1.5 minutes; hold at 90% mobile phase B for 1 minute and then drop back to 8% mobile phase B over 0.01 minute. Equilibrate system for 3 minutes. Total run time was 6 minutes. Within- and between-day assay precision was <9%, and within- and between-day assay accuracy was <9%.

Plasma noribogaine concentrations were determined in the 30 mg and 60 mg dose groups using a validated, sensitive LCMSMS method. Sample preparation involved deproteinization of plasma samples with acetonitrile and dilution of sample with 0.1% (v/v) formic acid. The compounds were separated by a 150×2.0 mm Luna 5 µm C18 column and detected with a triple-quadrupole API 4000 or 5000 mass spectrometer using electrospray ionization in positive mode and multiple reaction monitoring. Noribogaine-$d_4$ was used as the internal standard. The precursor-product ion transition values for noribogaine were m/z 297.6→122.3, and for the internal standard noribogaine-$d_4$ m/z 301.1→122.2. Analyst® software was used for data acquisition and processing. The ratio of the peak area of noribogaine to the internal standard noribogaine-$d_4$ was used for calibration and measurement of the unknown concentration of noribogaine. The LLOQ was 0.50 ng/ml noribogaine. The calibration curve was between 0.50 and 256.00 ng/ml noribogaine. Mobile phase was the same as method A, and binary flow was also the same as method A. The within- and between-day assay precision was <9%, and the within- and between-day assay accuracy was <9%.

Plasma noribogaine glucuronide concentrations were determined in the 30 mg and 60 mg dose groups using a validated sensitive LCMSMS method. Sample preparation involved deproteinization of plasma samples with acetonitrile, drying the samples under a stream of nitrogen and reconstitution of sample with acetonitrile:B.P. water (5:95, v/v) containing 0.1% (v/v) formic acid. The compounds were separated by a 150×2.0 mm Luna 5 µm C18 column and detected with a triple-quadrupole API 4000 or 5000 mass spectrometer using electrospray ionization in positive mode and multiple reaction monitoring. Noribogaine-$d_4$ was used as the internal standard. The precursor-product ion transition values for noribogaine glucuronide were m/z 472.8→297.3, and for the internal standard noribogaine-$d_4$ m/z 301.1→122.2. Analyst® software was used for data acquisition and processing. The ratio of the peak area of noribogaine glucuronide to the internal standard noribogaine-$d_4$ was used for calibration and measurement of the unknown concentration of noribogaine glucuronide. The LLOQ was 0.050 ng/ml noribogaine glucuronide. The calibration curve was between 0.050 and 6.400 ng/ml noribogaine glucuronide. Mobile phases was the same as method A. Binary flow: Initial concentration was 6% mobile phase B; hold at 6% mobile phase B for 0.5 minutes and linear rise to 90% mobile phase B over 2 minutes; hold at 90% mobile phase B for 1 minute and then drop back to 6% mobile phase B over 0.01 minute. Equilibrate system for 3.5 minutes. Total run time was 7 minutes. The within- and between-day assay precision was <11%, and the within- and between-day assay accuracy was <10%.

Urine noribogaine and noribogaine glucuronide concentrations were determined in the 30 mg and 60 mg dose groups using a validated sensitive LCMSMS method. Sample preparation involved deproteinization of urine samples with acetonitrile and dilution of the sample with 0.1% (v/v) formic acid. The compounds were separated by a 150×2.0 mm Luna 5 µm C18 column and detected with a triple-quadrupole API 4000 or 5000 mass spectrometer using electrospray ionization in positive mode and multiple reaction monitoring. Noribogaine-$d_4$ was used as the internal standard. The precursor-product ion transition values for noribogaine were m/z 297.6→122.3, noribogaine glucuronide m/z 472.8→297.3, and for the internal standard noribogaine-$d_4$ m/z 301.1→122.2. Analyst® software was used for data acquisition and processing. The ratios of the peak area of noribogaine and noribogaine glucuronide to the internal standard noribogaine-$d_4$ were used for calibration and measurement of the unknown concentration of noribogaine and its glucuronide. Assay LLOQ was 20.0 ng/ml for noribogaine and 2.0 ng/ml for noribogaine glucuronide. The calibration curve was between 20.0 and 5120.0 ng/ml noribogaine, and 2.0 and 512.0 ng/ml noribogaine glucuronide. Mobile phases were as described in method A, and binary flow as in method C. The within- and between-day assay precision was <13%, and within- and between-day assay accuracy was <12%.

Noribogaine and noribogaine glucuronide concentrations above the limit of quantification were used to calculate pharmacokinetic parameters using model-independent methods. The maximum plasma concentration (Cmax) and time to maximum plasma concentration (Tmax) were the observed values. Plasma concentration data in the post-distribution phase of the plasma concentration-time plot were fitted using linear regression to the formula ln C=ln Co−t.Kel, where Co was the zero-time intercept of the extrapolated terminal phase and Kel was the terminal elimination rate constant. The half-life ($t_{1/2}$) was determined using the formula $t_{1/2}$=0.693/Kel. The area under the concentration-time curve (AUC) from time zero to the last determined concentration-time point (tf) in the post distribution phase was calculated using the trapezoidal rule. The area under the curve from the last concentration-time point in the post distribution phase (Ctf) to time infinity was calculated from $AUC_{t\text{-}\infty}$=Ctf/Kel. The concentration used for Ctf was the last determined value above the LLOQ at the time point. The total $AUC_{0\text{-}\infty}$ was obtained by adding $AUC_{tf}$ and $AUC_{t\text{-}\infty}$. Noribogaine apparent clearance (CL/F) was determined using the formula CL/F=Dose/$AUC_{0\text{-}\infty}$×1000, and apparent volume of distribution (Vd/F) was determined using the formula Vd/F=(CL/F)/Kel. Total urine noribogaine was the sum of both analytes.

Summary statistics (means, standard deviations, and coefficients of variation) were determined for each dose group for safety laboratory test data, ECG and pharmacokinetic parameters, and pharmacodynamic variables. Categorical variables were analysed using counts and percentages. Dose-proportionality of AUC and Cmax was assessed using linear regression. The effect of dose on pharmacodynamic parameter values over time was assessed using two-factor analysis of variance (ANOVA). Pairwise comparisons (with Tukey-Kramer adjustment) between each dose group to the placebo were conducted at each time point using the least squares estimates obtained from the ANOVA, using SAS Proc Mixed (SAS ver 6.0).

Results

Pharmacokinetics: Mean plasma concentration-time plots of noribogaine are shown in FIG. 1, and mean pharmacokinetic parameters are shown in Table 1.

under fasting conditions were plotted. The mean $C_{max}$ of 5.2 ng/ml was observed 1.9 hours after administration, while the mean AUC/24 hr of 3.1 ng/ml was obtained.

The subject mean serum levels over time of noribogaine free base from a single dose of 10 mg noribogaine free base under fasting conditions were plotted. The mean $C_{max}$ of 14.5 ng/ml was observed 2.9 hours after administration, while the mean AUC/24 hr of 10.6 ng/ml was obtained.

The subject mean serum levels over time of noribogaine free base from a single dose of 30 mg noribogaine free base under fasting conditions were plotted. The mean $C_{max}$ of 55.9 ng/ml was observed between 1.75 hours after administration, while the mean AUC/24 of 29.2 ng/ml was obtained.

The subject mean serum levels over time of noribogaine free base from a single dose of 60 mg noribogaine free base under fasting conditions were plotted. The mean $C_{max}$ of 116

TABLE 1

|  | 3 mg (n = 6) (mean (SD)) | 10 mg (n = 6) (mean (SD)) | 30 mg (n = 6) (mean (SD)) | 60 mg (n = 6) (mean (SD) |
|---|---|---|---|---|
| Noribogaine | | | | |
| $AUC_{0-\infty}$ (ng · hr/ml) | 74.2 (13.1) | 254.5 (78.9) | 700.4 (223.3) | 1962.2 (726.5) |
| $AUC_{0-216}$ (ng · hr/ml) | 72.2 (13.2) | 251.4 (78.5) | 677.6 (221.1) | 1935.4 (725.4) |
| Cmax (ng/ml) | 5.2 (1.4) | 14.5 (2.1) | 55.9 (14.8) | 116.0 (22.5) |
| Tmax (hr) | 1.9 (0.6) | 2.9 (1.8) | 1.8 (0.6) | 2.4 (0.6) |
| $t_{1/2}$ (hr) | 40.9 (8.7) | 49.2 (11.5) | 27.6 (7.0)) | 29.1 (9.3) |
| Vd/F (L) | 2485.1 (801.5) | 3085.8 (1197.0) | 1850.8 (707.9) | 1416.8 (670.1) |
| CL/F (L/h) | 41.4 (7.0) | 42.3 (12.0) | 46.9 (16.4) | 34.0 (11.4) |
| Noribogaine glucuronide | | | | |
| $AUC_{0-\infty}$ (ng · hr/ml) | — | — | 25.8 (9.3) | 67.1 (21.9) |
| $AUC_{0-216}$ (ng · hr/ml) | — | — | 25.7 (9.1) | 65.0 (21.5) |
| Cmax (ng/ml) | — | — | 1.8 (0.6) | 4.1 (1.2) |
| Tmax (hr) | — | — | 3.0 (0.6) | 3.8 (1.2) |
| $t_{1/2}$ (hr) | — | — | 20.6 (4.9) | 23.1 (3.0) |

Noribogaine was rapidly absorbed, with peak concentrations occurring 2-3 hours after oral dosing. Fluctuations in individual distribution-phase concentration-time profiles may suggest the possibility of enterohepatic recirculation (see highlighted individual 4-8 hour profiles in FIG. 1, insert). Both Cmax and AUC increased linearly with dose (Table 1, upper panel). Mean half-life estimates of 28-50 hours were observed across dose groups for noribogaine. Volume of distribution was extensive (1417-3086 L across dose groups).

Figure 2:
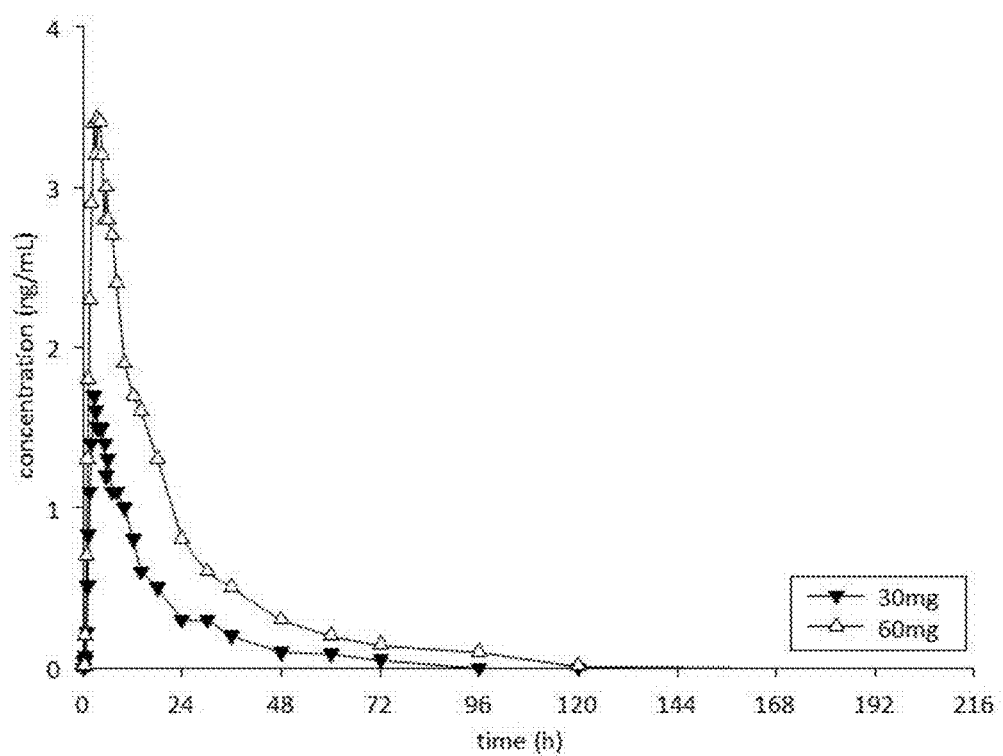
FIG. 2 represents mean plasma noribogaine glucuronide concentration-time profiles in healthy patients after single oral 30 or 60 mg doses.

Mean plasma noribogaine glucuronide concentration-time plots for the 30 mg and 60 mg dose group are shown in FIG. 2, and mean pharmacokinetic parameters are shown in Table 1, lower panel. Noribogaine glucuronide was detected in all subjects by 0.75 hours, with peak concentrations occurring 3-4 hours after noribogaine dosing. Mean half-life of 21-23 hours was estimated for plasma noribogaine glucuronide. The proportion of noribogaine glucuronide Cmax and AUC relative to noribogaine was 3-4% for both dose groups. Total urine noribogaine elimination was 1.16 mg and 0.82 mg for the 30 mg and 60 mg dose groups respectively, representing 3.9% and 1.4% of the doses administered.

The subject mean serum levels over time of noribogaine free base from a single dose of 3 mg noribogaine free base ng/ml was observed between 1.75 hours after administration, while the mean AUC/24 ng/ml of 61 was obtained.

The subject mean serum levels over time of noribogaine free base for all 4 cohorts were plotted. The extrapolated dosage of noribogaine free base required to provide a $C_{max}$ ranging from about 5.2 ng/ml to about 1980 ng/ml and an AUC/24 hr of about 3.1 ng/ml to about 1100 ng/ml was determined.

Pharmacodynamics: There was no evidence of pupillary constriction in subjects dosed with noribogaine. No between-dose group differences in pupil diameter were detected over time. After adjusting for baseline differences, comparison of each dose group with placebo by ANOVA showed no statistically significant differences (p>0.9).

Noribogaine treatment showed no analgesic effect in the cold pressor test. Analgesic effect was assessed based on duration of hand immersion in ice water and on visual analog scale (VAS) pain scores upon hand removal from the water bath. For duration of hand immersion, after adjusting for baseline differences, comparison of each dose group with placebo by ANOVA showed no statistically significant differences (p>0.9). Similarly, for VAS pain scores, after adjusting for baseline differences, comparison of each dose group with placebo by ANOVA showed no statistically significant differences (p=0.17).

Example 2

Safety and Tolerability of Noribogaine in Healthy Humans

Safety and tolerability of noribogaine were tested in the group of volunteers from Example 1. Cold pressor testing was conducted in 1° C. water according to the method of Mitchell et al. (*J Pain* 5:233-237, 2004) pre-dose, 6, 24, 48, 72 and 216 hours post-dosing. Safety evaluations included clinical monitoring, recording of adverse events (AEs), safety laboratory tests, vital signs, ECG telemetry from −2 h to 6 h after dosing, and 12-lead electrocardiograms (ECGs) up to 216 hours post-dosing.

Results

A total of thirteen adverse events were reported by seven participants (Table 2). Six adverse events were reported by three participants in the placebo group, five adverse events were reported by two subjects in the 3 mg dose group, and one adverse event was reported by single subjects in the 10 mg and 30 mg dose groups, respectively. The most common adverse events were headache (four reports) and epistaxis (two reports). All adverse events were of mild-moderate intensity, and all resolved prior to study completion. There were no changes in vital signs or safety laboratory tests of note. In particular, there were no changes in oximetry or capnography, or changes in respiratory rate. There were no QTcF values >500 msec at any time. One subject dosed with 10 mg noribogaine had a single increase in QTcF of >60 msec at 24 hours post-dosing.

TABLE 2

| Dose (mg) | Mild | Moderate | Severe |
|---|---|---|---|
| Placebo | Blepharitis<br>Bruising<br>Dry Skin<br>Eye pain, nonspecific<br>Infection at cannula site | Epistaxis | — |
| 3 | Back pain<br>Dizziness<br>Epistaxis<br>Headache | Headache | — |
| 10 | Headache | — | — |
| 30 | Headache | — | — |
| 60 | — | — | — |

Example 3

Safety, Tolerability, and Efficacy of Noribogaine in Opioid-Addicted Humans

This example is to illustrate that noribogaine can be administered at a therapeutic dosing while maintaining an acceptable QT interval. While the therapy employed is directed to opioid-dependent participants in a randomized, placebo-controlled, double-blind trial, the results show that a therapeutic window can be established for noribogaine.

The efficacy of noribogaine in humans was evaluated in opioid-dependent participants in a randomized, placebo-controlled, double-blind trial. Patients had been receiving methadone treatment as the opioid substitution therapy, but were transferred to morphine treatment prior to noribogaine administration. This was done to avoid negative noribogaine-methadone interactions that are not observed between noribogaine and morphine. See U.S. application Ser. No. 14/214,157, filed Mar. 14, 2014 and Ser. No. 14/346,655, filed Mar. 21, 2014, which are incorporated herein by reference in their entireties.

Three cohorts of nine (9) subjects (6 administered noribogaine and 3 administered placebo in each cohort) were evaluated for tolerability, pharmacokinetics, and efficacy. Cohort 1 received a single dose of 60 mg noribogaine or placebo. Cohort 2 received a single dose of 120 mg noribogaine or placebo. Cohort 3 received a single dose of 180 mg noribogaine or placebo. Treatment was administered 2 hours after last morphine dose and the time to resumption of morphine (opioid substitution treatment, OST) was determined. Few adverse effects of noribogaine were observed in any of the participants, including no hallucinatory effects. Table 3 shows the reported adverse events for each treatment that were not attributable to withdrawal from opioids. Headaches were frequent in the placebo and 60 mg noribogaine treatment groups, but were attenuated in the 120 mg and 180 mg dose groups.

TABLE 3

Treatment Emergent Adverse Events Summary

| System Organ Class<br>Preferred Term | Placebo<br>(N = 9) | 60 mg<br>(N = 6) | 120 mg<br>(N = 6) | 180 mg<br>(N = 6) |
|---|---|---|---|---|
| Number of Subjects Reporting any AEs | 19:7 (77.8%) | 15:5 (83.3%) | 28:6 (100.0%) | 17:4 (66.7%) |
| Ear and Labyrinth Disorders | 0 | 0 | 2:2 (33.3%) | 0 |
| Tinnitus | 0 | 0 | 2:2 (33.3%) | 0 |
| Eye Disorders | 2:2 (22.2%) | 3:3 (50.0%) | 5:5 (83.3%) | 5:4 (66.7%) |
| Visual Impairment | 2:2 (22.2%) | 2:2 (33.3%) | 5:5 (83.3%) | 5:4 (66.7%) |
| Dry Eye | 0 | 1:1 (16.7%) | 0 | 0 |
| Gastrointestinal Disorders | 3:2 (22.2%) | 2:2 (33.3%) | 7:2 (33.3%) | 4:2 (33.3%) |
| Nausea | 1:1 (11.1%) | 0 | 3:2 (33.3%) | 2:2 (33.3%) |
| Dry Mouth | 0 | 0 | 1:1 (16.7%) | 1:1 (16.7%) |
| Vomiting | 0 | 0 | 2:1 (16.7%) | 1:1 (16.7%) |
| Diarrhoea | 1:1 (11.1%) | 0 | 1:1 (16.7%) | 0 |
| Dyspepsia | 1:1 (11.1%) | 2:2 (33.3%) | 0 | 0 |
| General Disorders and Administration Site Conditions | 4:3 (33.3%) | 0 | 2:2 (33.3%) | 1:1 (16.7%) |
| Catheter Site Related Reaction | 0 | 0 | 0 | 1:1 (16.7%) |
| Catheter Site Pain | 3:2 (22.2%) | 0 | 2:2 (33.3%) | 0 |
| Malaise | 1:1 (11.1%) | 0 | 0 | 0 |
| Infections and Infestations | 1:1 (11.1%) | 0 | 1:1 (16.7%) | 2:2 (33.3%) |

TABLE 3-continued

Treatment Emergent Adverse Events Summary

| System Organ Class<br>Preferred Term | Placebo<br>(N = 9) | 60 mg<br>(N = 6) | 120 mg<br>(N = 6) | 180 mg<br>(N = 6) |
|---|---|---|---|---|
| Cellulitis | 0 | 0 | 1:1 (16.7%) | 1:1 (16.7%) |
| Urinary Tract Infection | 0 | 0 | 0 | 1:1 (16.7%) |
| Catheter Site Infection | 1:1 (11.1%) | 0 | 0 | 0 |
| Musculoskeletal and Connective Tissue Disorders | 1:1 (11.1%) | 2:1 (16.7%) | 0 | 2:2 (33.3%) |
| Back Pain | 1:1 (11.1%) | 2:1 (16.7%) | 0 | 1:1 (16.7%) |
| Limb Discomfort | 0 | 0 | 0 | 1:1 (16.7%) |
| Nervous System Disorders | 7:5 (55.6%) | 7:4 (66.7%) | 5:4 (66.7%) | 3:2 (33.3%) |
| Headache | 6:5 (55.6%) | 7:4 (66.7%) | 2:2 (33.3%) | 3:2 (33.3%) |
| Hyperaesthesia | 0 | 0 | 1:1 (16.7%) | 0 |
| Pseudoparalysis | 0 | 0 | 1:1 (16.7%) | 0 |
| Tremor | 0 | 0 | 1:1 (16.7%) | 0 |
| Somnoience | 1:1 (11.1%) | 0 | 0 | 0 |
| Psychiatric Disorders | 1:1 (11.1%) | 1:1 (16.7%) | 0 | 0 |
| Depressed Mood | 0 | 1:1 (16.7%) | 0 | 0 |
| Euphoric Mood | 1:1 (11.1%) | 0 | 0 | 0 |
| Respiratory, Thoracic and Mediastinal Disorders | 0 | 0 | 4:2 (33.3%) | 0 |
| Epistaxis | 0 | 0 | 2:1 (16.7%) | 0 |
| Oropharyngeal Pain | 0 | 0 | 1:1 (16.7%) | 0 |
| Rhinorrhoea | 0 | 0 | 1:1 (16.7%) | 0 |
| Skin and Subcutaneous Tissue Disorders | 0 | 0 | 2:1 (16.7%) | 0 |
| Skin Discomfort | 0 | 0 | 1:1 (16.7%) | 0 |
| Skin Irritation | 0 | 0 | 1:1 (16.7%) | 0 |

Note:
Within each system organ class, Preferred Terms are presented by descending incidence of descending dosages groups and then the placebo group.
Note:
N = number of subjects in the safety population.

Figure 3:
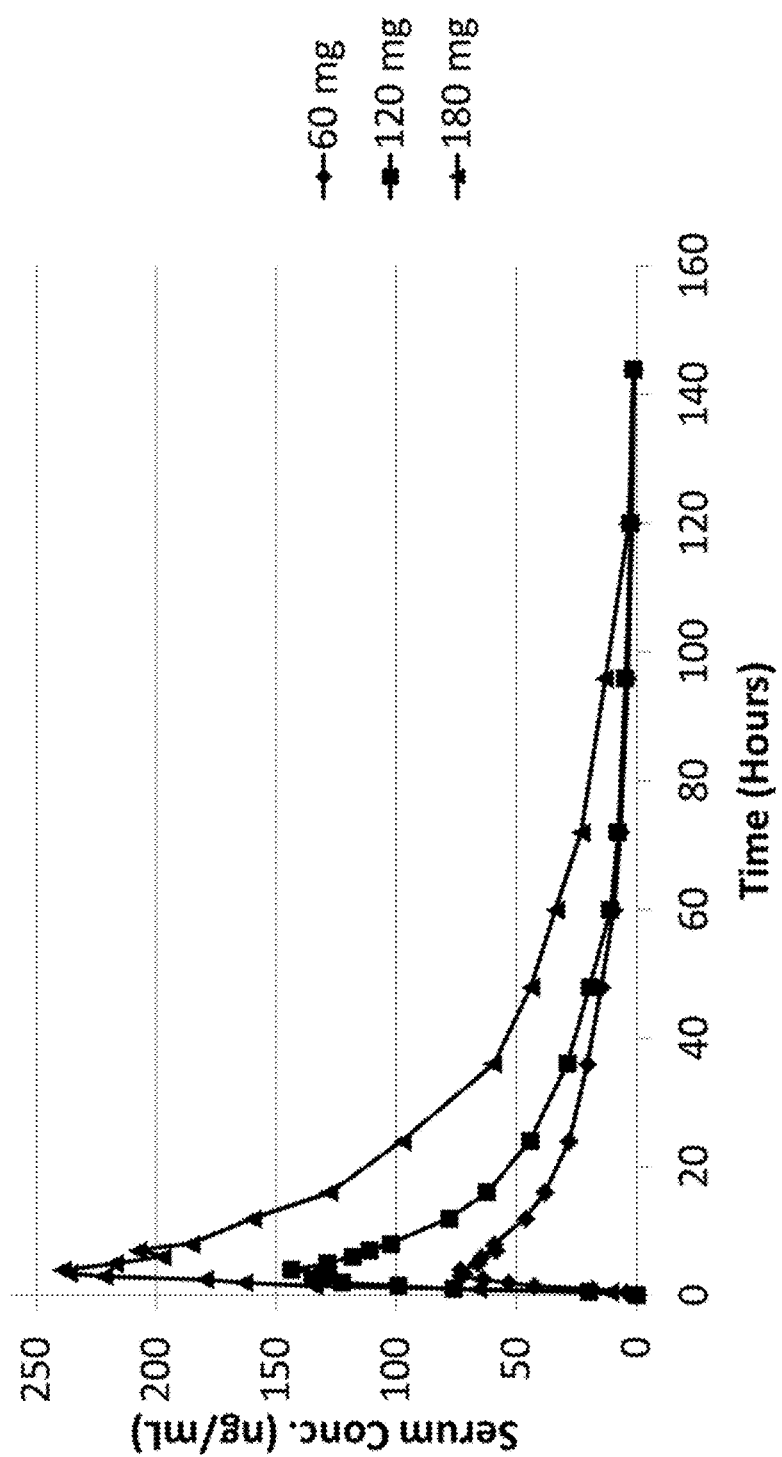
FIG. 3 illustrates the mean noribogaine concentration-time profile in opioid-addicted patients after a single oral 60 mg (diamonds), 120 mg (squares), or 180 mg (triangles) dose of noribogaine.

FIG. 3 indicates the average serum noribogaine concentration over time after administration of noribogaine for each cohort (60 mg, diamonds; 120 mg, squares; or 180 mg, triangles). Further results are detailed in U.S. Provisional Patent Application No. 62/023,100, filed Jul. 10, 2014, and titled "METHODS FOR ACUTE AND LONG-TERM TREATMENT OF DRUG ADDICTION," which is incorporated herein by reference in its entirety.

Results

Pharmacokinetic results for each cohort are given in Table 4. Maximum serum concentration of noribogaine (Cmax) increased in a dose-dependent manner. Time to Cmax (Tmax) was similar in all three cohorts. Mean half-life of serum noribogaine was similar to that observed in healthy patients.

Figure 4:
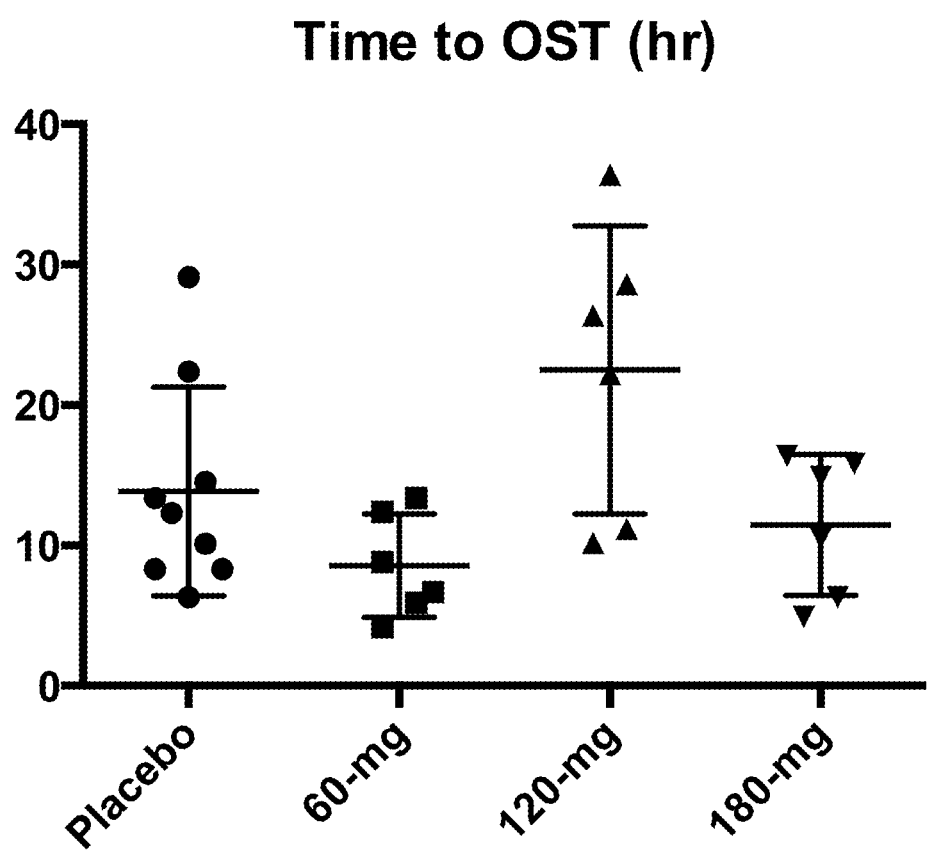
FIG. 4 illustrates hours to resumption of opioid substitution treatment (OST) for each patient given placebo (circles), or a single oral dose of noribogaine (60 mg, squares; 120 mg, triangles; 180 mg, inverted triangles). Center horizontal line represents mean. Error bars represent standard deviation.

FIG. 4 indicates the time to resumption of morphine (OST) for patients treated with placebo (circles), 60 mg noribogaine (squares), 120 mg noribogaine (triangles), and 180 mg noribogaine (inverted triangles). Patients receiving a single 120 mg dose of noribogaine exhibited an average time to resumption of opioids of greater than 20 hours. Patients receiving a single 180 mg dose of noribogaine exhibited an average time to resumption of opioids similar to that of placebo. This demonstrates that increasing the dose of noribogaine to 180 mg results in a shorter time to resumption of OST than observed in patients receiving 120 mg noribogaine. Time to resumption of OST after treatment with 180 mg was still longer than untreated patients (7 hours, not shown) or those administered 60 mg noribogaine.

TABLE 4

Pharmacokinetic results from the Patients in Phase IB Study

| PK parameter | Cohort 1 (60 mg)<br>Data (mean ± SD)<br>[range] | Cohort 2 (120 mg)<br>Data (mean ± SD)<br>[range] | Cohort 3 (180 mg)<br>Data (mean ± SD)<br>[range] |
|---|---|---|---|
| Cmax (ng/ml) | 81.64 ± 23.77<br>[41.29-113.21] | 172.79 ± 30.73<br>[138.84-229.55] | 267.88 ± 46.92<br>[204.85-338.21] |
| Tmax (hours) | 3.59 ± 0.92<br>[2.50-5.00] | 2.99 ± 1.23<br>[0.98-4.02] | 4.41 ± 1.80<br>[3.00-8.00] |
| $AUC_{(0-T)}$ (ng · hr/ml) | 2018.01 ± 613.91<br>[1094.46-2533.44] | 3226.38 ± 1544.26<br>[1559.37-5638.98] | 6523.28 ± 2909.80<br>[3716.69-10353.12] |
| $AUC_{(0-\infty)}$ (ng · hr/ml) | 2060.31 ± 609.39<br>[1122.29-2551.63] | 3280.50 ± 1581.43<br>[1595.84-5768.52] | 6887.67 ± 3488.91<br>[3734.21-12280.91] |
| Half-life (hrs) | 29.32 ± 7.28<br>[18.26-37.33] | 30.45 ± 9.14<br>[21.85-48.33] | 23.94 ± 5.54<br>[19.32-34.90] |
| Vd/F | 1440.7 ± 854.0<br>[619.5-2772.5] | 2106.43 ± 1644.54<br>[824.24-5243.78] | 1032.19 ± 365.30<br>[581.18-1608.98] |
| Cl/F | 32.14 ± 12.38<br>[23.51-53.46] | 44.68 ± 21.40<br>[20.80-75.20] | 31.47 ± 13.12<br>[14.66-48.20] |

Patients were evaluated based on the Clinical Opiate Withdrawal Scale (COWS), Subjective Opiate Withdrawal Scale (SOWS), and Objective Opiate Withdrawal Scale (OOWS) scoring systems over the period of time between administration of noribogaine (or placebo) until resumption of OST. These scales are outlined in Guidelines for the Psychosocially Assisted Pharmacological Treatment of Opioid Dependence, World Health Organization, Geneva (2009), Annex 10, which is incorporated herein by reference in its entirety. The scales measure the intensity of withdrawal symptoms, based on clinical, subjective, and objective indicia.

Figure 5:
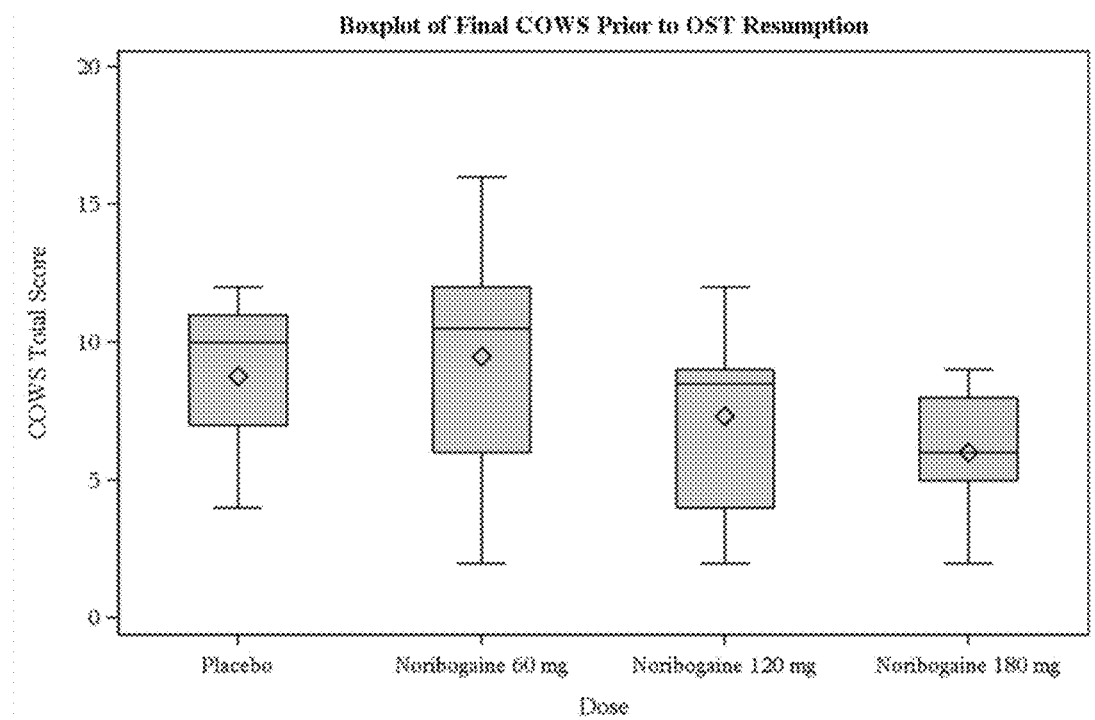
FIG. 5 illustrates results of noribogaine treatment on final COWS scores before resumption of OST. Boxes include values representing 25%-75% quartiles. Diamonds represent the median, crossbars represent mean. Whiskers represent values within one standard deviation of mid-quartiles. No outliers were present.

FIG. 5 shows the COWS scores at time of resumption of OST for each cohort. Box includes values representing 25%-75% quartiles. Diamond=median; crossbar in box=mean; whiskers=values within standard deviation of mid-quartiles. No outliers present. The highly variable COWS scores across and within each cohort indicates that patients were resuming opiates without relation to the intensity of withdrawal. This was also reflected in SOWS and OOWS scores at the time of resumption of OST.

Figure 6A:
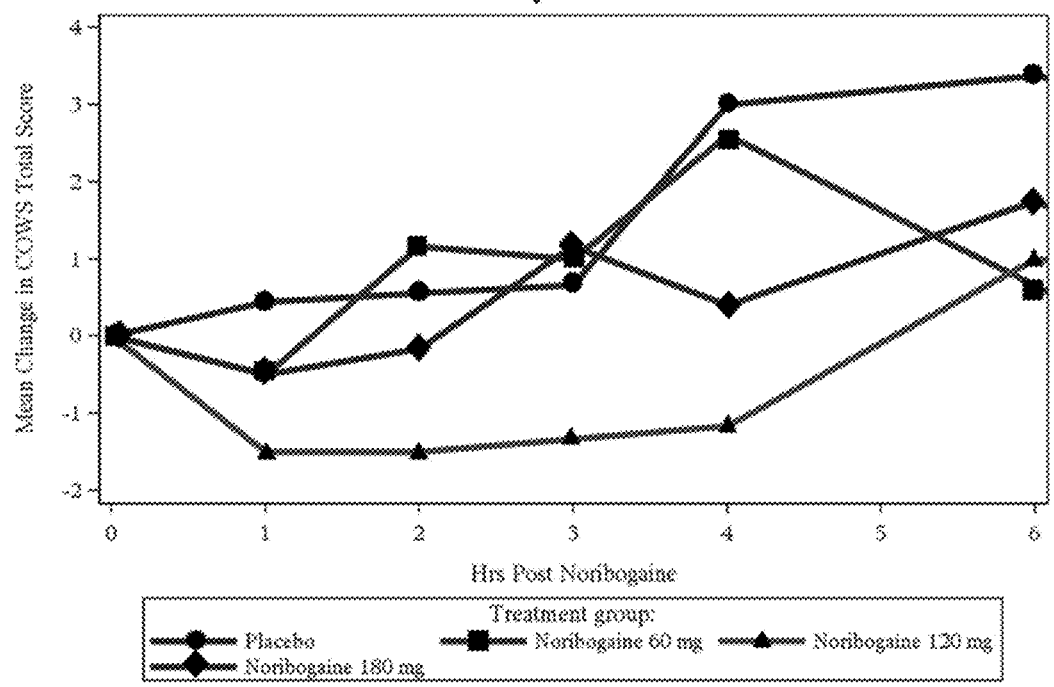
FIG. 6A illustrates of the mean change in total COWS scores over the first 6 hours following dosing of noribogaine (60 mg, squares; 120 mg, triangles; 180 mg, diamonds) or placebo (circles). Data is given relative to baseline COWS score.
Figure 6B:
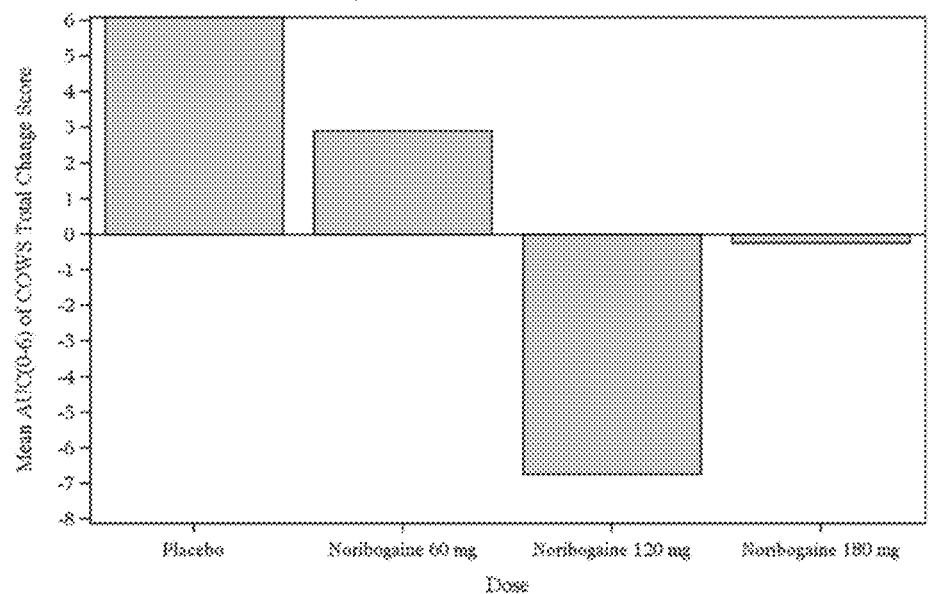
FIG. 6B illustrates the mean area under the curve (AUC) over the initial 6 hour period after administration of noribogaine or placebo, based on the COWS score data given in FIG. 6A. A negative change in score indicates that withdrawal symptoms subsided over the period.
Figure 7A:
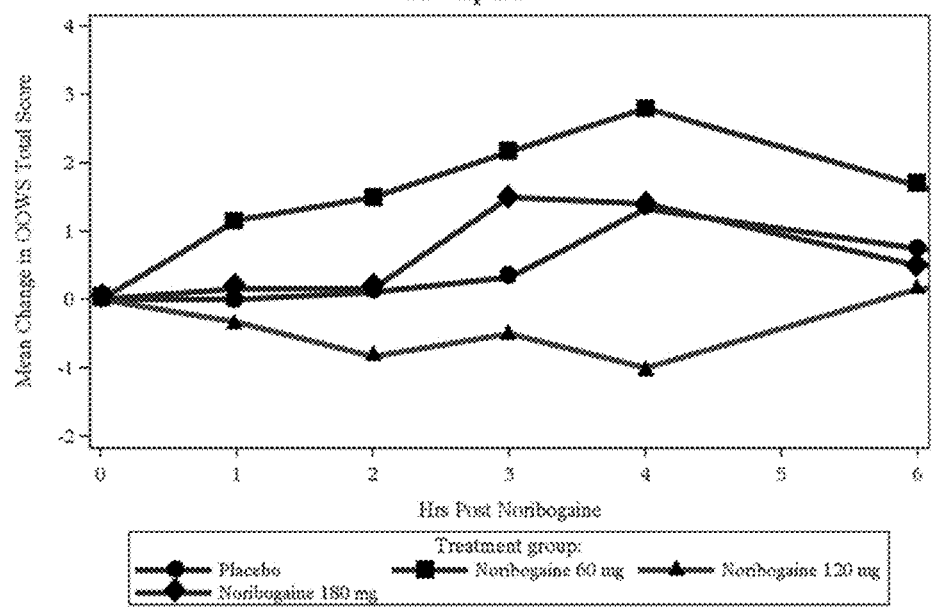
FIG. 7A illustrates of the mean change in total OOWS scores over the first 6 hours following dosing of noribogaine (60 mg, squares; 120 mg, triangles; 180 mg, diamonds) or placebo (circles). Data is given relative to baseline OOWS score.
Figure 7B:
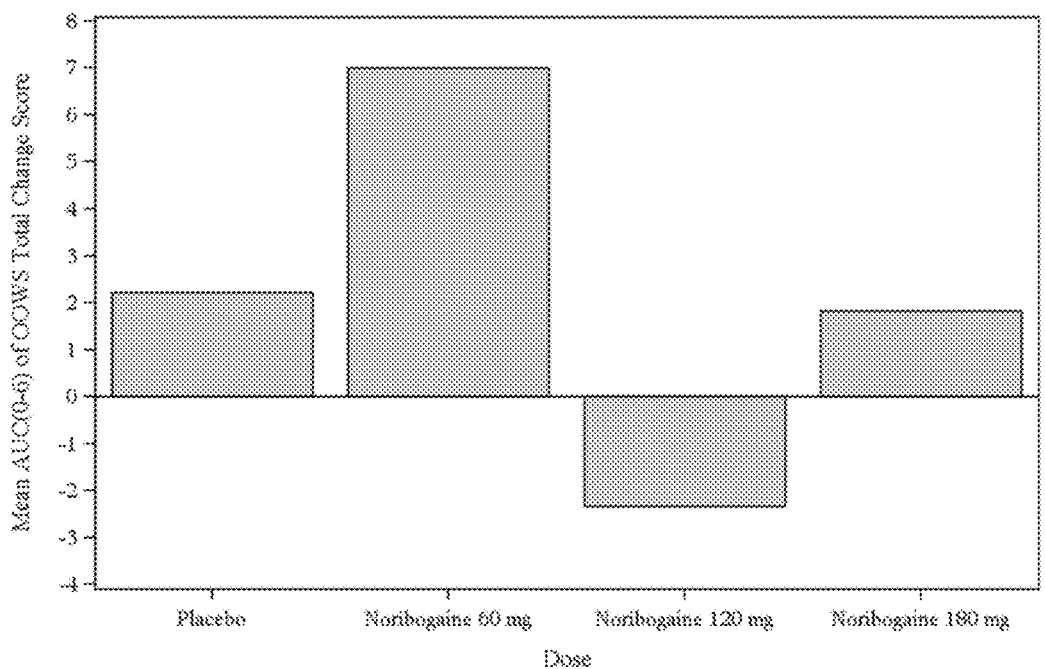
FIG. 7B illustrates the mean area under the curve (AUC) over the initial 6 hour period after administration of noribogaine or placebo, based on the OOWS score data given in FIG. 7A. A negative change in score indicates that withdrawal symptoms subsided over the period.
Figure 8A:
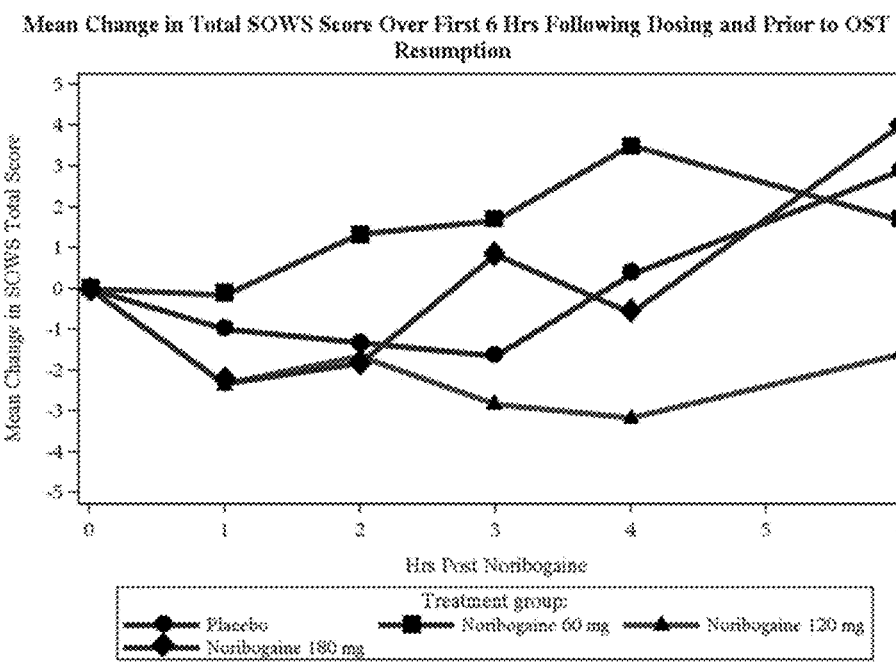
FIG. 8A illustrates of the mean change in total SOWS scores over the first 6 hours following dosing of noribogaine (60 mg, squares; 120 mg, triangles; 180 mg, diamonds) or placebo (circles). Data is given relative to baseline SOWS score.
Figure 8B:
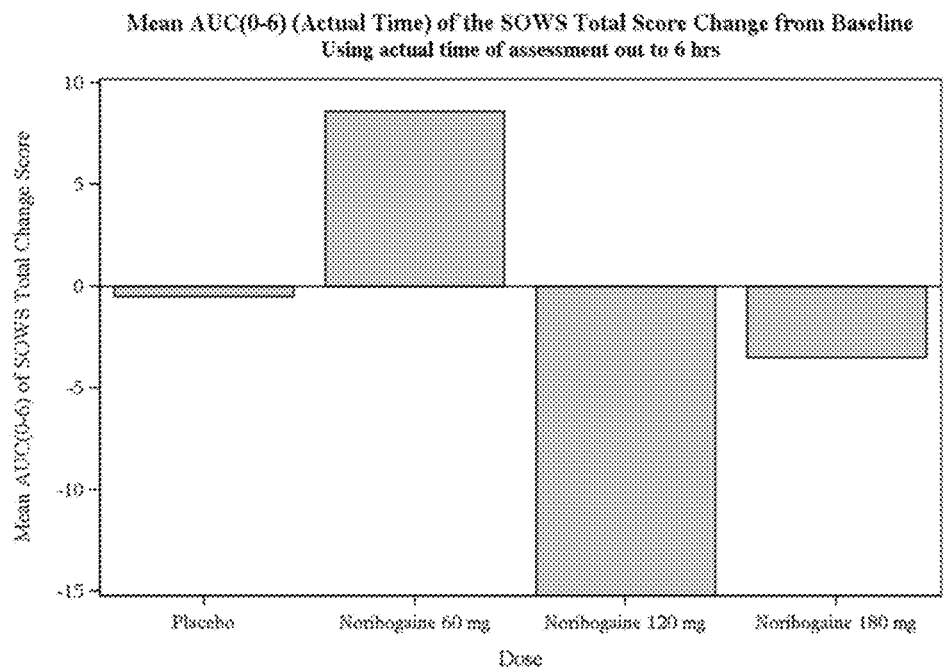
FIG. 8B illustrates the mean area under the curve (AUC) over the initial 6 hour period after administration of noribogaine or placebo, based on the SOWS score data given in FIG. 8A. A negative change in score indicates that withdrawal symptoms subsided over the period.

FIG. 6A shows the mean change in total COWS scores over the first six hours following dosing and prior to resumption of OST. FIG. 6B shows the mean AUC (0-6 hours) of the COWS total score change from baseline. FIG. 7A shows the mean change in total OOWS scores over the first six hours following dosing and prior to resumption of OST. FIG. 7B shows the mean AUC (0-6 hours) of the OOWS total score change from baseline. FIG. 8A shows the mean change in total SOWS scores over the first six hours following dosing and prior to resumption of OST. FIG. 8B shows the mean AUC (0-6 hours) of the SOWS total score change from baseline. These data indicate that withdrawal symptoms get worse over time after cessation of OST, and that patients administered placebo experience generally worse withdrawal symptoms over that period. Patients who received 120 mg noribogaine generally experienced fewer withdrawal symptoms than the other patients, regardless of the scale used. Patients administered placebo generally experienced more withdrawal symptoms than patients who were administered noribogaine.

Figure 9A:
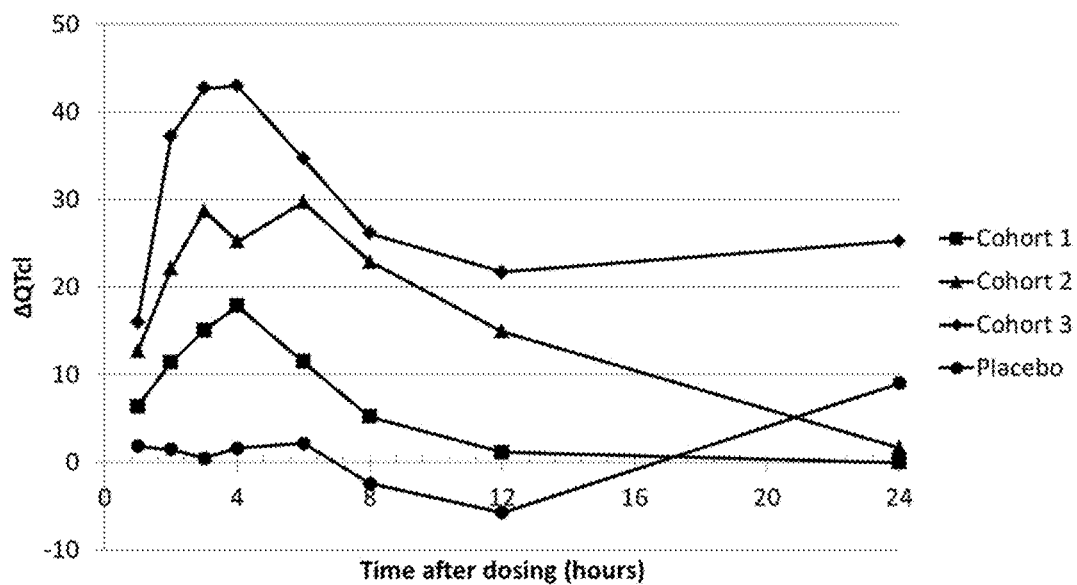
FIG. 9A illustrates the average change in QT interval (ΔQTcl) for each cohort (60 mg, squares; 120 mg, triangles; 180 mg, diamonds) or placebo (circles) over the first 24 hours post administration.
Figure 9B:
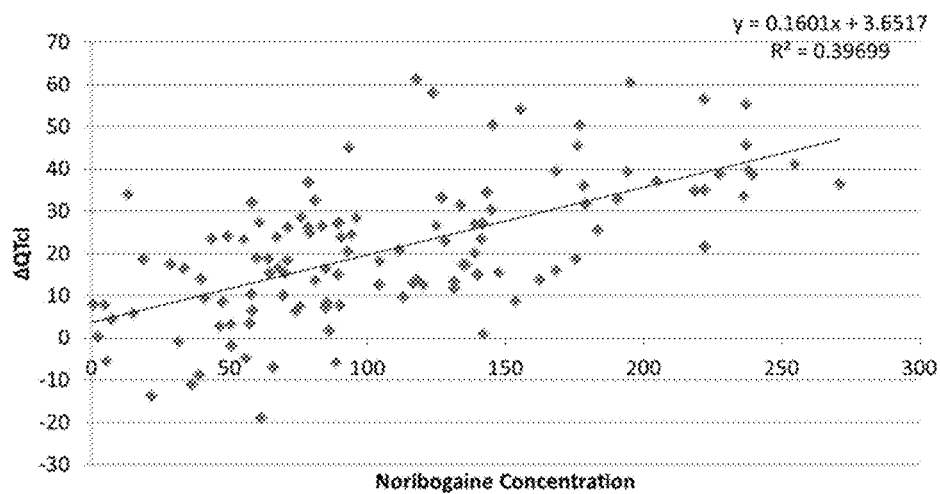
FIG. 9B illustrates the correlation between serum noribogaine concentration and ΔQTcl for each patient over time. The equation of the line is given.

Patients' QT intervals were evaluated at regular time points throughout the study. FIG. 9A shows the average change in QT interval (ΔQTcl, i.e., QT interval prolongation) over the first 24 hours post noribogaine (or placebo) administration. FIG. 9B shows the estimated correlation between noribogaine concentration and change in QT interval. There is a dose-dependent increase in QT interval prolongation that is correlated with the serum concentration of noribogaine.

Based on above data, it is believed that the therapeutic window for a single bolus dose of noribogaine is bound at the lower end by 50 mg and at the upper end by less than 180 mg. In particular, the therapeutic serum concentration in vivo appears to be between about 50 ng/mL and about 180 ng/mL.

Example 4

Effect of Noribogaine on Chronic Migraine in Humans

A female patient, age 25, with recurrent migraine headaches not attributable to withdrawal from opioids, is treated with noribogaine hydrochloride at a dose of about 1.5 mg/kg. During a period of several hours, her migraine symptoms are determined by self-evaluation and clinical evaluation.

What is claimed is:

1. A method for treating migraine headache and/or symptoms thereof in a patient in need thereof, comprising administering to the patient a therapeutically effective amount of noribogaine, an ester thereof, or a pharmaceutically acceptable salt of each thereof, wherein the therapeutically effective amount is sufficient to treat migraine headache and/or symptoms thereof while targeting a maximum QT interval prolongation of less than about 40 milliseconds during said treatment.

2. The method of claim 1, wherein the therapeutically effective amount is from about 50 ng to about 10 µg per kg body weight per day.

3. The method of claim 1, wherein the therapeutically effective amount is from about 1 mg to about 4 mg per kg body weight per day.

4. The method of claim 1, wherein the noribogaine, ester thereof, or pharmaceutically acceptable salt of each thereof is administered by sublingual, buccal, intranasal, or intrapulmonary delivery.

5. The method of claim 1, wherein the therapeutically effective amount is administered once a day.

6. The method of claim 1, wherein the therapeutically effective amount is administered two or more times per day.

7. A method for preventing migraine headache and/or symptoms thereof in a patient in need thereof, comprising administering to the patient a prophylactically effective amount of noribogaine, an ester thereof, or a pharmaceutically acceptable salt of each thereof, said amount being sufficient to prevent migraine headache and/or symptoms thereof while targeting a maximum QT interval prolongation of less than about 40 milliseconds during said treatment.

8. The method of claim 7, wherein said prophylactically effective amount is from about 50 ng to about 10 µg per kg body weight per day.

9. The method of claim 7, wherein said prophylactically effective amount is less than about 90% of the therapeutically effective amount.

10. The method of claim 7, wherein the noribogaine, ester thereof, or pharmaceutically acceptable salt of each thereof is administered by sublingual, intranasal, buccal, or intrapulmonary delivery.

11. The method of claim 7, wherein the noribogaine, ester thereof, or pharmaceutically acceptable salt of each thereof is administered on an as-needed basis as determined by the subject.

12. The method of claim 1, wherein the patient's QT interval is not prolonged by more than about 30 ms.

13. The method of claim 1, further comprising administering at least one agent known to treat and/or prevent migraine and/or symptoms thereof.

14. The method of claim 13, wherein the at least one agent is selected from the group consisting of: an analgesic, a triptan, an ergotamine, and dexamethasone.

15. The method of claim 1, wherein noribogaine or the pharmaceutically acceptable salt thereof is administered.

* * * * *